(12) United States Patent
Hanssen et al.

(10) Patent No.: US 10,098,743 B2
(45) Date of Patent: Oct. 16, 2018

(54) PROSTHETIC IMPLANT SUPPORT STRUCTURE

(75) Inventors: Arlen D. Hanssen, Rochester, MN (US); David Lewallen, Rochester, MN (US)

(73) Assignee: Zimmer, Inc., Warsaw, IN (US)

( * ) Notice: Subject to any disclaimer, the term of this patent is extended or adjusted under 35 U.S.C. 154(b) by 258 days.

(21) Appl. No.: 13/619,091

(22) Filed: Sep. 14, 2012

(65) Prior Publication Data

US 2013/0013078 A1   Jan. 10, 2013

Related U.S. Application Data

(60) Continuation of application No. 12/946,132, filed on Nov. 15, 2010, now Pat. No. 8,728,168, which is a
(Continued)

(51) Int. Cl.
*A61F 2/34* (2006.01)
*A61F 2/30* (2006.01)
(Continued)

(52) U.S. Cl.
CPC ............ *A61F 2/30* (2013.01); *A61F 2/30734* (2013.01); *A61F 2/34* (2013.01); *A61F 2/36* (2013.01); *A61B 17/86* (2013.01); *A61F 2/30767* (2013.01); *A61F 2/30771* (2013.01); *A61F 2/30965* (2013.01); *A61F 2/3662* (2013.01);
(Continued)

(58) Field of Classification Search
CPC ................ A61F 2/34; A61F 2002/3445; A61F 2002/3448; A61F 2002/345; A61F 2002/347; A61F 2002/3479; A61F 2002/3482; A61F 2002/3485;
(Continued)

(56) References Cited

U.S. PATENT DOCUMENTS 2,947,308 A   8/1960 Gorman
3,605,123 A   9/1971 Hahn
(Continued)

FOREIGN PATENT DOCUMENTS

AU   2004203348 A1   9/2005
CA      2473633 A1   9/2005
(Continued)

OTHER PUBLICATIONS

US 5,536,414, 10/1994, Cohen et al. (withdrawn)
(Continued)

*Primary Examiner* — Paul Prebilic
(74) *Attorney, Agent, or Firm* — Schwegman Lundberg & Woessner, P.A.

(57) ABSTRACT

A prosthetic system that includes a prosthetic implant and a support structure secured to an inner surface of a cavity of a bone is disclosed. The support structure defines a channel that extends through the length of the support structure. The prosthetic implant is received in the channel, and a portion of the prosthetic implant is secured to an inner surface of the support structure by an adhesive. The support structure may comprise a pair of partially hemispherical components arranged in spaced apart relationship thereby defining the channel between the pair of components.

35 Claims, 9 Drawing Sheets

Related U.S. Application Data continuation of application No. 11/560,276, filed on Nov. 15, 2006, which is a division of application No. 10/225,774, filed on Aug. 22, 2002.

(60) Provisional application No. 60/315,148, filed on Aug. 27, 2001.

(51) Int. Cl.
  *A61F 2/36* (2006.01)
  *A61B 17/86* (2006.01)
  *A61F 2/38* (2006.01)
  *A61F 2/28* (2006.01)
  *A61F 2/46* (2006.01)

(52) U.S. Cl.
  CPC ....... *A61F 2/389* (2013.01); *A61F 2002/2835* (2013.01); *A61F 2002/30131* (2013.01); *A61F 2002/30228* (2013.01); *A61F 2002/30233* (2013.01); *A61F 2002/30235* (2013.01); *A61F 2002/30248* (2013.01); *A61F 2002/30276* (2013.01); *A61F 2002/30278* (2013.01); *A61F 2002/30299* (2013.01); *A61F 2002/30324* (2013.01); *A61F 2002/30354* (2013.01); *A61F 2002/30449* (2013.01); *A61F 2002/30606* (2013.01); *A61F 2002/30616* (2013.01); *A61F 2002/30736* (2013.01); *A61F 2002/30738* (2013.01); *A61F 2002/30777* (2013.01); *A61F 2002/30784* (2013.01); *A61F 2002/30841* (2013.01); *A61F 2002/30878* (2013.01); *A61F 2002/3403* (2013.01); *A61F 2002/3611* (2013.01); *A61F 2002/3625* (2013.01); *A61F 2002/3631* (2013.01); *A61F 2002/4631* (2013.01); *A61F 2002/4681* (2013.01); *A61F 2220/005* (2013.01); *A61F 2220/0033* (2013.01); *A61F 2230/0013* (2013.01); *A61F 2230/0069* (2013.01); *A61F 2230/0071* (2013.01); *A61F 2230/0086* (2013.01); *A61F 2230/0093* (2013.01); *A61F 2250/0036* (2013.01); *A61F 2310/00017* (2013.01); *A61F 2310/00023* (2013.01); *A61F 2310/00029* (2013.01); *A61F 2310/00131* (2013.01); *A61F 2310/00203* (2013.01); *A61F 2310/00239* (2013.01)

(58) Field of Classification Search
  CPC ........ A61F 2002/3487; A61F 2002/349; A61F 2002/3495
  USPC .................. 623/22.11, 22.17, 22.19, 22.21, 623/22.23–22.28, 22.32, 22.33, 22.35, 623/22.39, 908; 606/287, 286, 91, 99
  See application file for complete search history.

(56) References Cited

U.S. PATENT DOCUMENTS

| | | | |
|---|---|---|---|
| 3,658,056 A | 4/1972 | Huggler et al. | |
| D230,429 S | 2/1974 | Davidson et al. | |
| 3,855,638 A | 12/1974 | Pilliar | |
| 3,871,031 A | 3/1975 | Boutin | |
| 3,891,997 A | 7/1975 | Herbert | |
| 3,903,549 A | 9/1975 | Deyerle | |
| 3,906,550 A | 9/1975 | Rostoker et al. | |
| 3,918,102 A | 11/1975 | Eichler | |
| 4,064,567 A | 12/1977 | Burstein et al. | |
| 4,136,405 A | 1/1979 | Pastrick et al. | |
| 4,164,794 A | 8/1979 | Spector et al. | |
| 4,206,516 A | 6/1980 | Pilliar | |
| 4,216,549 A | 8/1980 | Hillberry et al. | |
| 4,219,893 A | 9/1980 | Noiles | |
| 4,224,696 A | 9/1980 | Murray et al. | |
| 4,404,691 A | 9/1983 | Buning et al. | |
| 4,444,061 A | 4/1984 | Mathias | |
| 4,523,587 A | 6/1985 | Frey | |
| 4,549,319 A | 10/1985 | Meyer | |
| 4,550,448 A * | 11/1985 | Kenna ................. A61F 2/30767 606/76 |
| 4,566,138 A | 1/1986 | Lewis et al. | |
| 4,659,331 A | 4/1987 | Matthews et al. | |
| 4,662,891 A | 5/1987 | Noiles | |
| 4,678,470 A | 7/1987 | Nashef et al. | |
| 4,693,721 A * | 9/1987 | Ducheyne ........... A61F 2/30907 419/24 |
| 4,711,639 A | 12/1987 | Grundei | |
| 4,718,909 A | 1/1988 | Brown | |
| 4,735,625 A | 4/1988 | Davidson | |
| 4,778,473 A | 10/1988 | Matthews et al. | |
| 4,789,663 A | 12/1988 | Wallace et al. | |
| 4,790,852 A | 12/1988 | Noiles | |
| 4,822,366 A | 4/1989 | Bolesky | |
| 4,827,919 A | 5/1989 | Barbarito et al. | |
| 4,828,565 A | 5/1989 | Duthoit et al. | |
| 4,834,759 A | 5/1989 | Spotorno et al. | |
| 4,840,632 A | 6/1989 | Kampner | |
| 4,865,607 A | 9/1989 | Witzel et al. | |
| 4,878,919 A | 11/1989 | Pavlansky et al. | |
| 4,883,448 A | 11/1989 | Kobayashi et al. | |
| 4,883,488 A | 11/1989 | Bloebaum et al. | |
| 4,888,021 A | 12/1989 | Forte et al. | |
| 4,936,859 A | 6/1990 | Morscher et al. | |
| 4,938,769 A | 7/1990 | Shaw | |
| 4,944,757 A | 7/1990 | Martinez et al. | |
| 4,950,298 A | 8/1990 | Gustilo et al. | |
| 4,960,427 A * | 10/1990 | Noiles ....................... 623/22.18 |
| 4,988,359 A | 1/1991 | Frey et al. | |
| 5,019,103 A | 5/1991 | Van Zile et al. | |
| 5,032,134 A | 7/1991 | Lindwer | |
| 5,059,196 A | 10/1991 | Coates | |
| 5,092,897 A | 3/1992 | Forte | |
| 5,108,446 A | 4/1992 | Wagner et al. | |
| 5,133,771 A | 7/1992 | Duncan et al. | |
| 5,152,797 A | 10/1992 | Luckman et al. | |
| 5,156,626 A | 10/1992 | Broderick et al. | |
| 5,163,966 A | 11/1992 | Norton et al. | |
| 5,176,711 A | 1/1993 | Grimes | |
| 5,192,329 A * | 3/1993 | Christie et al. ............ 623/22.22 |
| 5,197,488 A | 3/1993 | Kovacevic | |
| 5,211,664 A | 5/1993 | Tepic et al. | |
| 5,222,984 A | 6/1993 | Forte | |
| 5,226,915 A | 7/1993 | Bertin | |
| 5,246,459 A | 9/1993 | Elias | |
| 5,370,693 A | 6/1994 | Kelman et al. | |
| 5,356,414 A | 10/1994 | Cohen et al. | |
| 5,356,629 A | 10/1994 | Sander et al. | |
| 5,358,527 A | 10/1994 | Forte | |
| 5,358,530 A | 10/1994 | Hodorek | |
| 5,376,123 A | 12/1994 | Klaue et al. | |
| 5,387,241 A | 2/1995 | Hayes | |
| 5,405,394 A | 4/1995 | Davidson | |
| 5,413,604 A | 5/1995 | Hodge | |
| 5,443,512 A | 8/1995 | Parr et al. | |
| 5,462,563 A | 10/1995 | Shearer et al. | |
| 5,480,444 A | 1/1996 | Incavo | |
| 5,480,445 A | 1/1996 | Burkinshaw | |
| 5,489,311 A | 2/1996 | Cipolletti | |
| 5,507,830 A | 4/1996 | DeMane et al. | |
| 5,510,396 A | 4/1996 | Prewett et al. | |
| 5,531,791 A | 7/1996 | Wolfinbarger, Jr. | |
| 5,549,685 A | 8/1996 | Hayes | |
| 5,571,198 A | 11/1996 | Drucker | |
| 5,591,233 A | 1/1997 | Kelman et al. | |
| 5,609,645 A | 3/1997 | Vinciuerra | |
| 5,658,338 A | 8/1997 | Tullos et al. | |
| 5,658,349 A | 8/1997 | Brooks et al. | |
| 5,662,158 A | 9/1997 | Caldarise | |
| 5,683,467 A | 11/1997 | Pappas | |
| 5,702,478 A | 12/1997 | Tornier | |
| 5,702,483 A | 12/1997 | Kwong | |

(56) References Cited

U.S. PATENT DOCUMENTS

| | | |
|---|---|---|
| 5,734,959 A | 3/1998 | Krebs et al. |
| 5,766,256 A | 6/1998 | Oudard et al. |
| 5,782,925 A | 7/1998 | Collazo et al. |
| 5,782,929 A | 7/1998 | Sederholm |
| 5,788,976 A | 8/1998 | Bradford |
| 5,824,103 A | 10/1998 | Williams et al. |
| 5,858,020 A | 1/1999 | Johnson et al. |
| 5,871,548 A | 2/1999 | Sanders et al. |
| 5,879,393 A | 3/1999 | Whiteside et al. |
| 5,910,172 A | 6/1999 | Penenberg |
| 5,931,409 A | 8/1999 | Nulle et al. |
| 5,957,979 A | 9/1999 | Beckman et al. |
| 5,958,314 A | 9/1999 | Draenert |
| 5,972,368 A | 10/1999 | McKay |
| 5,976,148 A | 11/1999 | Charpenet et al. |
| 5,984,968 A | 11/1999 | Park |
| 5,993,716 A | 11/1999 | Draenert |
| 5,997,581 A | 12/1999 | Khalili |
| 6,008,432 A | 12/1999 | Taylor |
| 6,013,080 A | 1/2000 | Khalili |
| 6,039,764 A | 3/2000 | Pottenger et al. |
| 6,042,612 A | 3/2000 | Voydeville |
| 6,053,945 A | 4/2000 | O'Neil et al. |
| 6,074,423 A | 6/2000 | Lawson |
| 6,074,424 A | 6/2000 | Perrone, Jr. et al. |
| 6,080,195 A | 6/2000 | Colleran et al. |
| 6,117,175 A | 9/2000 | Bosredon |
| 6,126,691 A | 10/2000 | Kasra et al. |
| 6,136,029 A | 10/2000 | Johnson et al. |
| 6,139,581 A | 10/2000 | Engh et al. |
| 6,139,584 A | 10/2000 | Ochoa et al. |
| 6,142,998 A | 11/2000 | Smith et al. |
| 6,162,254 A | 12/2000 | Timoteo |
| 6,162,255 A | 12/2000 | Oyola |
| 6,171,342 B1 | 1/2001 | O'Neil et al. |
| 6,264,699 B1 | 7/2001 | Noiles et al. |
| 6,290,725 B1 | 9/2001 | Weiss et al. |
| 6,294,187 B1 * | 9/2001 | Boyce et al. ................. 424/422 |
| 6,328,764 B1 | 12/2001 | Mady |
| 6,355,069 B1 | 3/2002 | DeCarlo, Jr. et al. |
| 6,368,352 B1 | 4/2002 | Camino et al. |
| 6,423,096 B1 | 7/2002 | Musset et al. |
| 6,428,578 B2 | 8/2002 | White |
| 6,447,549 B1 | 9/2002 | Taft |
| 6,458,161 B1 | 10/2002 | Gibbs et al. |
| 6,613,092 B1 | 9/2003 | Kana et al. |
| 6,682,568 B2 * | 1/2004 | Despres et al. ............ 623/22.42 |
| 6,699,293 B2 | 3/2004 | White |
| 6,797,006 B2 | 9/2004 | Hodorek |
| 6,843,806 B2 | 1/2005 | Hayes et al. |
| 6,875,218 B2 | 4/2005 | Dye et al. |
| 6,875,237 B2 | 4/2005 | Dye et al. |
| 6,926,740 B2 | 8/2005 | Lewis et al. |
| 6,946,001 B2 | 9/2005 | Sanford et al. |
| 6,981,991 B2 | 1/2006 | Ferree |
| 7,105,026 B2 | 9/2006 | Johnson et al. |
| 7,179,295 B2 | 2/2007 | Kovacevic |
| 7,179,296 B2 | 2/2007 | Dooney |
| 7,179,297 B2 | 2/2007 | McLean |
| 7,179,298 B2 | 2/2007 | Greenlee |
| D538,431 S | 3/2007 | Botha |
| 7,238,208 B2 | 7/2007 | Camino et al. |
| 7,264,636 B2 | 9/2007 | Lewis et al. |
| 7,291,174 B2 | 11/2007 | German et al. |
| 7,291,177 B2 | 11/2007 | Gibbs |
| 7,435,263 B2 | 10/2008 | Barnett et al. |
| 7,713,306 B2 | 5/2010 | Gibbs |
| D618,800 S | 6/2010 | Mayon et al. |
| 7,846,212 B2 | 12/2010 | Lewis et al. |
| 7,892,288 B2 | 2/2011 | Blaylock et al. |
| 7,892,289 B2 | 2/2011 | Serafin, Jr. et al. |
| 8,123,814 B2 | 2/2012 | Meridew et al. |
| 8,382,849 B2 | 2/2013 | Thomas |
| D684,693 S | 6/2013 | Hanssen et al. |
| 8,506,645 B2 | 8/2013 | Blaylock et al. |
| 8,535,385 B2 | 9/2013 | Hanssen et al. |
| 8,728,168 B2 * | 5/2014 | Hanssen et al. ............ 623/22.24 |
| 9,044,326 B2 | 6/2015 | Blaylock et al. |
| 9,192,476 B2 * | 11/2015 | Thomas ............... A61F 2/30767 |
| 9,265,614 B2 | 2/2016 | Blaylock et al. |
| 2002/0072802 A1 | 6/2002 | O'Neil et al. |
| 2002/0151984 A1 | 10/2002 | White |
| 2003/0065397 A1 | 4/2003 | Hanssen et al. |
| 2003/0153981 A1 | 8/2003 | Wang et al. |
| 2003/0163203 A1 | 8/2003 | Nycz et al. |
| 2003/0183025 A1 | 10/2003 | Krstic |
| 2003/0229398 A1 | 12/2003 | Iesaka |
| 2004/0034432 A1 | 2/2004 | Hughes et al. |
| 2004/0049270 A1 | 3/2004 | Gerwitz |
| 2004/0049284 A1 | 3/2004 | German et al. |
| 2004/0117024 A1 | 6/2004 | Gerbec et al. |
| 2004/0162619 A1 | 8/2004 | Blaylock et al. |
| 2004/0172137 A1 | 9/2004 | Blaylock et al. |
| 2005/0107883 A1 | 5/2005 | Goodfried et al. |
| 2005/0278034 A1 | 12/2005 | Johnson et al. |
| 2005/0283254 A1 | 12/2005 | Hayes, Jr. et al. |
| 2007/0088443 A1 | 4/2007 | Hanssen et al. |
| 2007/0129809 A1 | 6/2007 | Meridew et al. |
| 2008/0167722 A1 | 7/2008 | Metzger et al. |
| 2008/0281430 A1 | 11/2008 | Kelman et al. |
| 2010/0145452 A1 | 6/2010 | Blaylock et al. |
| 2011/0066252 A1 | 3/2011 | Hanssen et al. |
| 2011/0112651 A1 | 5/2011 | Blaylock et al. |
| 2011/0295382 A1 | 12/2011 | Hanssen |
| 2013/0013080 A1 | 1/2013 | Hanssen et al. |
| 2013/0018478 A1 | 1/2013 | Hanssen et al. |
| 2013/0253658 A1 | 9/2013 | Despres et al. |
| 2013/0304221 A1* | 11/2013 | Blaylock et al. ............ 623/20.32 |
| 2014/0039638 A1* | 2/2014 | Meridew et al. ............ 623/22.28 |
| 2014/0081418 A1* | 3/2014 | Hanssen et al. ............ 623/23.44 |
| 2014/0249637 A1 | 9/2014 | Hanssen et al. |
| 2015/0257890 A1* | 9/2015 | Blaylock ............... A61F 2/30734 623/20.16 |
| 2016/0058560 A1 | 3/2016 | Blaylock et al. |
| 2016/0184103 A1* | 6/2016 | Fonte ................... A61L 27/306 623/23.5 |

FOREIGN PATENT DOCUMENTS

| | | |
|---|---|---|
| DE | 102010044571 A1 | 3/2012 |
| EP | 0336774 B1 | 12/1992 |
| EP | 0532585 B1 | 4/2000 |
| EP | 1004283 A2 | 5/2000 |
| EP | 0863731 B1 | 4/2001 |
| EP | 1004283 A3 | 3/2002 |
| EP | 1004283 B1 | 5/2005 |
| EP | 1913902 A1 | 4/2008 |
| EP | 2130518 A1 | 12/2009 |
| FR | 2702651 A1 | 9/1994 |
| FR | 2772593 A1 | 6/1999 |
| GB | 2223172 A | 4/1990 |
| JP | 6169930 A | 6/1994 |
| JP | 10277069 A | 10/1998 |
| JP | 2000185062 A | 7/2000 |
| JP | 2001503283 A | 3/2001 |
| JP | 2001526573 A | 12/2001 |
| JP | 2004016822 A | 1/2004 |
| JP | 2005246036 A | 9/2005 |
| WO | WO-9730661 A1 | 8/1997 |
| WO | WO-9852499 A1 | 11/1998 |
| WO | WO-9932053 A1 | 7/1999 |
| WO | WO-0205732 A1 | 1/2002 |
| WO | WO-2009089581 A1 | 7/2009 |
| WO | WO-2013134333 A1 | 9/2013 |

OTHER PUBLICATIONS

"U.S. Appl. No. 10/225,774, Advisory Action dated Oct. 26, 2005", 3 pgs.

"U.S. Appl. No. 10/225,774, Examiner Interview Summary dated Mar. 17, 2005", 4 pgs.

"U.S. Appl. No. 10/225,774, Final Office Action dated Jun. 6, 2005", 9 pgs.

(56) References Cited

OTHER PUBLICATIONS

"U.S. Appl. No. 10/225,774, Final Office Action dated Aug. 17, 2006", 8 pgs.
"U.S. Appl. No. 10/225,774, Non-Final Office Action dated Feb. 8, 2006", 6 pgs.
"U.S. Appl. No. 10/225,774, Non-Final Office Action dated Jun. 30, 2004", 5 pgs.
"U.S. Appl. No. 10/225,774, Non-Final Office Action dated Dec. 8, 2004", 6 pgs.
"U.S. Appl. No. 10/225,774, Response filed Mar. 7, 2005 to Non-Final Office Action dated Dec. 8, 2004", 21 pgs.
"U.S. Appl. No. 10/225,774, Response filed Apr. 16, 2004 to Restriction Requirement dated Mar. 17, 2004", 1 pg.
"U.S. Appl. No. 10/225,774, Response filed Jun. 7, 2006 to Non-Final Office Action dated Feb. 8, 2006", 21 pgs.
"U.S. Appl. No. 10/225,774, Response filed Sep. 20, 2004 to Non-Final Office Action dated Jun. 30, 2004", 14 pgs.
"U.S. Appl. No. 10/225,774, Response filed Oct. 6, 2005 to Final Office Action dated Jun. 6, 2005", 21 pgs.
"U.S. Appl. No. 10/225,774, Response filed Nov. 15, 2006 to Final Office Action dated Aug. 17, 2006", 1 pg.
"U.S. Appl. No. 10/225,774, Restriction Requirement dated Mar. 17, 2004", 6 pgs.
"U.S. Appl. No. 10/780,378, Final Office Action dated Apr. 20, 2010", 7 pgs.
"U.S. Appl. No. 10/780,378, Final Office Action dated Aug. 21, 2008", 8 pgs.
"U.S. Appl. No. 10/780,378, Final Office Action dated Aug. 27, 2007", 7 pgs.
"U.S. Appl. No. 10/780,378, Non Final Office Action dated Feb. 2, 2009", 7 pgs.
"U.S. Appl. No. 10/780,378, Non Final Office Action dated Mar. 30, 2007", 7 pgs.
"U.S. Appl. No. 10/780,378, Non Final Office Action dated Dec. 12, 2007", 8 pgs.
"U.S. Appl. No. 10/780,378, Preliminary Amendment filed Jun. 1, 2004", 20 pgs.
"U.S. Appl. No. 10/780,378, Response filed Jan. 8, 2007 to Restriction Requirement dated Dec. 4, 2006", 1 pg.
"U.S. Appl. No. 10/780,378, Response filed May 28, 2008 to Non-Final Office Action dated Dec. 12, 2007", 11 pgs.
"U.S. Appl. No. 10/780,378, Response filed Jun. 15, 2007 to Non-Final Office Action dated Mar. 30, 2007", 7 pgs.
"U.S. Appl. No. 10/780,378, Response filed Jun. 24, 2009 to Non-Final Office Action dated Feb. 2, 2009", 15 pgs.
"U.S. Appl. No. 10/780,378, Response filed Sep. 19, 2006 to Restriction Requirement dated Aug. 25, 2006", 1 pg.
"U.S. Appl. No. 10/780,378, Response filed Oct. 31, 2007 to Final Office Action dated Aug. 27, 2007", 8 pgs.
"U.S. Appl. No. 10/780,378, Response filed Nov. 12, 2008 to Final Office Action dated Aug. 21, 2008", 10 pgs.
"U.S. Appl. No. 10/780,378, Response filed Dec. 22, 2009 to Restriction Requirement dated Oct. 22, 2009", 2 pgs.
"U.S. Appl. No. 10/780,378, Restriction Requirement dated Dec. 4, 2006", 6 pgs.
"U.S. Appl. No. 10/780,378, Restriction Requirement dated Aug. 25, 2006", 6 pgs.
"U.S. Appl. No. 10/780,378, Restriction Requirement dated Oct. 22, 2009", 7 pgs.
"U.S. Appl. No. 10/794,721, Final Office Action dated Jan. 16, 2008", 8 pgs.
"U.S. Appl. No. 10/794,721, Final Office Action dated Jan. 16, 2009", 6 pgs.
"U.S. Appl. No. 10/794,721, Final Office Action dated May 6, 2010", 8 pgs.
"U.S. Appl. No. 10/794,721, Non Final Office Action dated Jul. 8, 2008", 6 pgs.
"U.S. Appl. No. 10/794,721, Non Final Office Action dated Aug. 3, 2007", 7 pgs.
"U.S. Appl. No. 10/794,721, Non Final Office Action dated Nov. 2, 2006", 7 pgs.
"U.S. Appl. No. 10/794,721, Non-Final Office Action dated Jun. 15, 2009", 9 pgs.
"U.S. Appl. No. 10/794,721, Notice of Allowance dated Oct. 14, 2010", 6 pgs.
"U.S. Appl. No. 10/794,721, Response filed Feb. 2, 2007 to Non Final Office Action dated Nov. 2, 2006", 7 pgs.
"U.S. Appl. No. 10/794,721, Response filed Apr. 14, 2009 to Final Office Action dated Jan. 16, 2009", 8 pgs.
"U.S. Appl. No. 10/794,721, Response filed Jun. 16, 2008 to Final Office Action dated Jan. 16, 2008", 8 pgs.
"U.S. Appl. No. 10/794,721, Response filed Sep. 28, 2009 to Non Final Office Action dated Jun. 15, 2009", 10 pgs.
"U.S. Appl. No. 10/794,721, Response filed Oct. 6, 2010 to Final Office Action dated May 6, 2010", 6 pgs.
"U.S. Appl. No. 10/794,721, Response filed Oct. 8, 2008 to Non Final Office Action dated Jul. 8, 2008", 8 pgs.
"U.S. Appl. No. 10/794,721, Response filed Nov. 8, 2007 to Non Final Office Action dated Aug. 3, 2007", 7 pgs.
"U.S. Appl. No. 10/794,721, Supplemental Response filed Feb. 8, 2010 to Non Final Office Action dated Jan. 12, 2010", 2 pgs.
"U.S. Appl. No. 10/794,721, Supplemental Response filed May 18, 2007 to Non Final Office Action dated Nov. 2, 2006", 7 pgs.
"U.S. Appl. No. 11/560,276, Examiner Interview Summary dated Jan. 18, 2012", 4 pgs.
"U.S. Appl. No. 11/560,276, Examiner Interview Summary dated Jun. 5, 2012", 3 pgs.
"U.S. Appl. No. 11/560,276, Final Office Action dated Mar. 27, 2012", 8 pgs.
"U.S. Appl. No. 11/560,276, Final Office Action dated Oct. 8, 2010", 6 pgs.
"U.S. Appl. No. 11/560,276, Non Final Office Action dated Mar. 3, 2010", 8 pgs.
"U.S. Appl. No. 11/560,276, Non Final Office Action dated Aug. 11, 2011", 6 pgs.
"U.S. Appl. No. 11/560,276, Response filed Feb. 7, 2011 to Final Office Action dated Oct. 8, 2010", 10 pgs.
"U.S. Appl. No. 11/560,276, Response filed Feb. 13, 2012 to Non Final Office Action dated Aug. 11, 2011", 13 pgs.
"U.S. Appl. No. 11/560,276, Response filed Jun. 27, 2012 to Final Office Action dated Mar. 27, 2012", 12 pgs.
"U.S. Appl. No. 11/560,276, Response filed Aug. 2, 2010 to Non Final Office Action dated Mar. 3, 2010", 12 pgs.
"U.S. Appl. No. 11/560,276, Response filed Oct. 21, 2009 to Restriction Requirement dated Aug. 21, 2009", 12 pgs.
"U.S. Appl. No. 11/560,276, Restriction Requirement dated Aug. 21, 2009", 7 pgs.
"U.S. Appl. No. 12/886,297, Final Office Action dated Nov. 16, 2012", 6 pgs.
"U.S. Appl. No. 12/886,297, Non Final Office Action dated Jun. 21, 2012", 10 pgs.
"U.S. Appl. No. 12/886,297, Response filed May 7, 2012 to Restriction Requirement dated Mar. 6, 2012", 2 pgs.
"U.S. Appl. No. 12/886,297, Response filed Oct. 22, 2012 to Non Final Office Action dated Jun. 21, 2012", 19 pgs.
"U.S. Appl. No. 12/886,297, Restriction Requirement dated Mar. 6, 2012", 6 pgs.
"U.S. Appl. No. 12/946,132, Examiner Interview Summary dated Jun. 5, 2012", 3 pgs.
"U.S. Appl. No. 12/946,132, Final Office Action dated Jul. 25, 2012", 12 pgs.
"U.S. Appl. No. 12/946,132, Non Final Office Action dated Mar. 28, 2012", 10 pgs.
"U.S. Appl. No. 12/946,132, Response filed Jun. 27, 2012 to Non Final Office Action dated Mar. 28, 2012", 15 pgs.
"U.S. Appl. No. 12/946,132, Response filed Sep. 6, 2011 to Restriction Requirement dated Aug. 23, 2011", 8 pgs.
"U.S. Appl. No. 12/946,132, Response filed Sep. 24, 2012 to Final Office Action dated Jul. 25, 2012", 16 pgs.
"U.S. Appl. No. 12/946,132, Restriction Requirement dated Aug. 23, 2011", 8 pgs.

(56) References Cited

OTHER PUBLICATIONS

"U.S. Appl. No. 13/007,225, Non Final Office Action dated Nov. 19, 2012", 9 pgs.
"U.S. Appl. No. 13/007,225, Preliminary Amendment filed Jan. 14, 2011", 4 pgs.
"U.S. Appl. No. 13/007,225, Response filed Oct. 22, 2012 to Restriction Requirement dated Sep. 20, 2012", 10 pgs.
"U.S. Appl. No. 13/007,225, Restriction Requirement dated Sep. 20, 2012", 8 pgs.
"U.S. Appl. No. 13/007,225, Supplemental Preliminary Amendment filed Sep. 23, 2011", 8 pgs.
"U.S. Appl. No. 13/205,163, Preliminary Amendment filed Aug. 8, 2011", 8 pgs.
"U.S. Appl. No. 13/619,190, Preliminary Amendment filed Oct. 29, 2012", 8 pgs.
"U.S. Appl. No. 29/379,094, Application filed Nov. 15, 2010", 6 pgs.
"U.S. Appl. No. 29/379,094, Response filed Nov. 21, 2012 to Restriction Requirement dated Oct. 23, 2012", 4 pgs.
"U.S. Appl. No. 29/379,094, Restriction Requirement dated Oct. 23, 2012", 7 pgs.
"Australian Application No. 2004203348, Office Action dated Jan. 13, 2010", 3 pgs.
"Canadian Application No. 2,473,633, Office Action dated Mar. 12, 2010", 3 pgs.
"European Application No. 04254352.0, European Search Report dated Jun. 22, 2005", 3 pgs.
"Japanese Application No. 2004-216179, Office Action dated May 26, 2009", 8 pgs.
"U.S. Appl. No. 12/886,297, Examiners Interview Summary dated May 6, 2013", 3 pgs.
"U.S. Appl. No. 12/886,297, Non Final Office Action dated Apr. 22, 2013", 6 pgs.
"U.S. Appl. No. 12/886,297, Notice of Allowance dated Feb. 22, 2013", 10 pgs.
"U.S. Appl. No. 12/886,297, Notice of Allowance dated Jun. 26, 2013", 10 pgs.
"U.S. Appl. No. 12/886,297, Preliminary Amendment filed Sep. 20, 2010", 10 pgs.
"U.S. Appl. No. 13/007,225, Examiner Interview Summary dated May 30, 2013", 23 pgs.
"U.S. Appl. No. 13/007,225, Final Office Action dated Apr. 18, 2013", 10 pgs.
"U.S. Appl. No. 13/007,225, Response filed Mar. 12, 2013 to Non-Final Office Action dated Nov. 19, 2012", 13 pgs.
"U.S. Appl. No. 13/007,225, Response filed Jul. 18, 2013 to Final Office Action dated Apr. 18, 2013", 15 pgs.
"U.S. Appl. No. 13/205,163, Non Final Office Action dated Apr. 4, 2013", 8 pgs.
"U.S. Appl. No. 13/205,163, Response filed Feb. 21, 2013 to Restriction Requirement dated Jan. 24, 2013", 10 pgs.
"U.S. Appl. No. 13/205,163, Response filed Jul. 3, 2013 to Non Final Office Action dated Apr. 4, 2013", 13 pgs.
"U.S. Appl. No. 13/205,163, Restriction Requirement dated Jan. 24, 2013", 6 pgs.
"U.S. Appl. No. 13/416,857, Response filed May 24, 2013 to Non Final Office Action dated Feb. 25, 2013", 15 pgs.
"U.S. Appl. No. 29/379,094, Notice of Allowance dated Feb. 28, 2013", 12 pgs.
"European Application Serial No. 04254352.0, Examination Notification Art. 94(3) dated Apr. 22, 2013", 5 pgs.
"Forbes Magazine Ranks Zimmer Holdings Among the 'Best Managed Companies in America'", PR Newswire, (Jan. 23, 2004), 2 pgs.
"International Application Serial No. PCT/US2013/029251, International Search Report dated Jun. 19, 2013", 5 pgs.
"International Application Serial No. PCT/US2013/029251, Written Opinion dated Jun. 19, 2013", 7 pgs.
U.S. Appl. No. 29/369,066, filed Sep. 1, 2010, Prosthetic Implant Support Structure.
U.S. Appl. No. 10/225,774, filed Aug. 22, 2002, Prosthetic Implant Support Structure.
U.S. Appl. No. 11/560,276, filed Nov. 15, 2006, Prosthetic Implant Support Structure.
U.S. Appl. No. 12/946,132, filed Nov. 15, 2010, Prosthetic Implant Support Structure.
U.S. Appl. No. 13/205,163, filed Aug. 8, 2011, Prosthetic Implant Support Structure.
U.S. Appl. No. 29/379,094, filed Nov. 15, 2010, Prosthetic Implant Support Structure.
U.S. Appl. No. 12/702,861, filed Feb. 9, 2010, Prosthetic Implant Support Structure.
U.S. Appl. No. 13/619,190, filed Sep. 14, 2012, Prosthetic Implant Support Structure.
U.S. Appl. No. 10/794,721, U.S. Pat. No. 7,892,288, filed Mar. 5, 2004, Femoral Augments for Use With Knee Joint Prosthesis.
U.S. Appl. No. 13/619,134, filed Sep. 14, 2012, Prosthetic Implant Support Structure.
U.S. Appl. No. 13/007,225, filed Jan. 14, 2011, Femoral Augments for Use With Knee Joint Prosthesis.
U.S. Appl. No. 10/780,378, filed Feb. 17, 2004, Prosthetic Implant Support Structure.
U.S. Appl. No. 12/886,297, filed Sep. 20, 2010, Tibial Augments for Use With Knee Joint Prostheses, Method of Implanting the Tibial Augment, and Associated Tools.
"U.S. Appl. No. 11/560,276, Final Office Action dated Oct. 17, 2013", 12 pgs.
"U.S. Appl. No. 12/946,132, Non Final Office Action dated Oct. 11, 2013", 7 pgs.
"U.S. Appl. No. 13/619,134, Restriction Requirement dated Oct. 17, 2013", 5 pgs.
"U.S. Appl. No. 13/619,190, Restriction Requirement dated Oct. 18, 2013", 7 pgs.
"European Application Serial No. 04254352.0, Response filed Sep. 2, 2013 to Examination Notification Art. 94(3) dated Apr. 22, 2013", 10 pgs.
U.S. Appl. No. 11/560,276, Response filed Dec. 17, 2013 to Final Office Action, 11 pgs.
"U.S. Appl. No. 11/560,276, Non Final Office Action dated Jan. 22, 2014", 10 pgs.
"U.S. Appl. No. 12/946,132, Notice of Allowance dated Mar. 27, 2014", 6 pgs.
U.S. Appl. No. 12/946,132, Response filed Feb. 11, 2014 to Non-Final Office Action, 19 pgs.
"U.S. Appl. No. 13/007,225, Non Final Office Action dated Jan. 29, 2014", 11 pgs.
"U.S. Appl. No. 13/619,134, Non Final Office Action dated Dec. 13, 2013", 9 pgs.
U.S. Appl. No. 13/619,134, Response filed Nov. 8, 2013 to Restriction Requirement, 8 pgs.
"U.S. Appl. No. 13/619,190, Non Final Office Action dated Dec. 18, 2013", 11 pgs.
U.S. Appl. No. 13/619,190, Response filed Nov. 18, 2013 to Restriction requirement, 7 pgs.
"European Application Serial No. 04254352.0, Examination Notification Art. 94(3) dated Mar. 10, 2014", 5 pgs.
"U.S. Appl. No. 11/560,276, Final Office Action dated Jun. 25, 2014", 10 pgs.
"U.S. Appl. No. 11/560,276, Response filed May 22, 2014 to Non Final Office Action dated Jan. 22, 2014", 10 pgs.
"U.S. Appl. No. 13/007,225, Final Office Action dated Jun. 25, 2014", 11 pgs.
"U.S. Appl. No. 13/007,225, Response filed May 29, 2014 to Non Final Office Action dated Jan. 29, 2014", 12 pgs.
"U.S. Appl. No. 13/619,134, Advisory Action dated Sep. 18, 2014", 3 pgs.
"U.S. Appl. No. 13/619,134, Final Office Action dated May 8, 2014", 10 pgs.
"U.S. Appl. No. 13/619,134, Response filed Apr. 14, 2014 to Non-Final Office Action dated Dec. 13, 2013", 11 pgs.
"U.S. Appl. No. 13/619,134, Response filed Sep. 8, 2014 to Final Office Action dated May 8, 2014", 13 pgs.

(56) References Cited

OTHER PUBLICATIONS

"U.S. Appl. No. 13/619,134, Response filed Oct. 9, 2014 to Advisory Action dated Sep. 18, 2014", 14 pgs.
"U.S. Appl. No. 13/619,190, Final Office Action dated Jun. 25, 2014", 10 pgs.
"U.S. Appl. No. 13/619,190, Response filed May 19, 2014 to Non Final Office Action dated Dec. 18, 2013", 12 pgs.
"U.S. Appl. No. 13/619,190, Supplemental Preliminary Amendment filed Apr. 15, 2013", 8 pgs.
"U.S. Appl. No. 14/278,916, Preliminary Amendment", 4 pgs, dated Jul. 9, 2014.
"U.S. Appl. No. 14/278,916, Supplemental Preliminary Amendment filed Jul. 18, 2014", 7 pgs.
"International Application Serial No. PCT/US2013/029251, International Preliminary Report on Patentability dated Sep. 18, 2014", 9 pgs.
"U.S. Appl. No. 11/560,276, Non Final Office Action dated Dec. 5, 2014", 14 pgs.
"U.S. Appl. No. 11/560,276, Response filed Oct. 27, 2014 to Final Office Action dated Jun. 25, 2014", 13 pgs.
"U.S. Appl. No. 13/007,225, Non Final Office Action dated Dec. 11, 2014", 6 pgs.
"U.S. Appl. No. 13/007,225, Response filed Oct. 27, 2014 to Final Office Action dated Jun. 25, 2014", 16 pgs.
"U.S. Appl. No. 13/619,134, Non Final Office Action dated Dec. 5, 2014", 18 pgs.
"U.S. Appl. No. 13/619,190, Non Final Office Action dated Dec. 4, 2014", 14 pgs.
"U.S. Appl. No. 13/619,190, Response filed Oct. 27, 2014 to Final Office Action dated Jun. 25, 2014", 13 pgs.
"U.S. Appl. No. 11/560,276, Final Office Action dated May 1, 2015", 16 pgs.
"U.S. Appl. No. 11/560,276, Response filed Apr. 6, 2015 to Non-Final Office Action dated Dec. 5, 2014", 16 pgs.
"U.S. Appl. No. 13/007,225, Notice of Allowance dated Apr. 6, 2015", 10 pgs.
"U.S. Appl. No. 13/007,225, Response filed Mar. 3, 2015 to Non-Final Office Action dated Dec. 11, 2014", 13 pgs.
"U.S. Appl. No. 13/619,134, Final Office Action dated Mar. 10, 2015", 20 pgs.
"U.S. Appl. No. 13/619,134, Response filed Jan. 22, 2015 to Non-Final Office Action dated Dec. 5, 2014", 32 pgs.
"U.S. Appl. No. 13/619,190, Final Office Action dated May 12, 2015", 16 pgs.
"U.S. Appl. No. 13/619,190, Response filed Apr. 6, 2015 to Non-Final Office Action dated Dec. 4, 2014", 17 pgs.
"U.S. Appl. No. 13/944,441, Non Final Office Action dated Apr. 20, 2015", 12 pgs.
"U.S. Appl. No. 13/944,441, Response filed Mar. 30, 2015 to Restriction Requirement dated Feb. 2, 2015", 8 pgs.
"U.S. Appl. No. 13/944,441, Restriction Requirement dated Feb. 2, 2015", 6 pgs.
"U.S. Appl. No. 14/085,040, Restriction Requirement dated Apr. 22, 2015", 6 pgs.
"U.S. Appl. No. 14/278,916, Non Final Office Action dated May 11, 2015", 9 pgs.
"U.S. Appl. No. 11/560,276, Non Final Office Action dated Sep. 25, 2015", 16 pgs.
"U.S. Appl. No. 11/560,276, Response filed Sep. 1, 2015 to Final Office Action dated May 1, 2015", 28 pgs.
"U.S. Appl. No. 13/619,134, Non Final Office Action dated Jul. 6, 2015", 19 pgs.
"U.S. Appl. No. 13/619,134, Response filed Jun. 10, 2015 to Non-Final Office Action dated Mar. 10, 2015", 33 pgs.
"U.S. Appl. No. 13/619,190, Non Final Office Action dated Sep. 25, 2015", 17 pgs.
"U.S. Appl. No. 13/619,190, Response filed Sep. 1, 2015 to Final Office Action dated May 12, 2015", 30 pgs.
"U.S. Appl. No. 13/944,441, Final Office Action dated Sep. 17, 2015", 7 pgs.
"U.S. Appl. No. 13/944,441, Notice of Allowance dated Oct. 14, 2015", 8 pgs.
"U.S. Appl. No. 13/944,441, Preliminary Amendment filed Jul. 19, 2013", 8 pgs.
"U.S. Appl. No. 13/944,441, Response filed Aug. 20, 2015 to Non Final Office Action dated Apr. 20, 2015", 16 pgs.
"U.S. Appl. No. 13/944,441, Response filed Oct. 5, 2015 to Final Office Action dated Sep. 17, 2015", 8 pgs.
"U.S. Appl. No. 14/085,040, Non Final Office Action dated Jul. 21, 2015", 12 pgs.
"U.S. Appl. No. 14/085,040, Response filed Oct. 21, 2015 to Non Final Office Action dated Jul. 21, 2015", 34 pgs.
"U.S. Appl. No. 14/085,040, Response to Restriction Requirement filed Jun. 22, 2015 to Restriction Requirement dated Apr. 22, 2015", 8 pgs.
"U.S. Appl. No. 14/278,916, Response filed Sep. 10, 2015 to Non Final Office Action dated May 11, 2015", 11 pgs.
"U.S. Appl. No. 14/722,701, Preliminary Amendment filed Jun. 16, 2015", 9 pgs.
"U.S. Appl. No. 11/560,276, Final Office Action dated Feb. 26, 2016", 17 pgs.
"U.S. Appl. No. 11/560,276, Response filed Jan. 25, 2016 to Non-Final Office Action dated Sep. 25, 2015", 33 pgs.
"U.S. Appl. No. 13/619,134, Appeal Brief filed Feb. 4, 2016", 72 pgs.
"U.S. Appl. No. 13/619,134, Final Office Action dated Dec. 2, 2015", 21 pgs.
"U.S. Appl. No. 13/619,134, Non Final Office Action dated Jun. 22, 2016", 24 pgs.
"U.S. Appl. No. 13/619,134, Response filed Nov. 10, 2015 to Non Final Office Action dated Jul. 6, 2015", 39 pgs.
"U.S. Appl. No. 13/619,190, Final Office Action dated Mar. 1, 2016", 18 pgs.
"U.S. Appl. No. 13/619,190, Response filed Jan. 25, 2016 to Non-Final Office Action dated Sep. 25, 2015", 35 pgs.
"U.S. Appl. No. 13/619,190, Response filed Sep. 1, 2016 to Final Office Action dated Mar. 1, 2016", 29 pgs.
"U.S. Appl. No. 14/085,040, Final Office Action dated Nov. 12, 2015", 14 pgs.
"U.S. Appl. No. 14/085,040, Non Final Office Action dated Mar. 28, 2016", 10 pgs.
"U.S. Appl. No. 14/085,040, Notice of Allowance dated Aug. 31, 2016", 6 pgs.
"U.S. Appl. No. 14/085,040, Response filed Mar. 7, 2016 to Final Office Action dated Nov. 12, 2015", 7 pgs.
"U.S. Appl. No. 14/085,040, Response filed Jul. 28, 2016 to Non Final Office Action dated Mar. 28, 2016", 11 pgs.
"U.S. Appl. No. 14/278,916, Non Final Office Action dated May 25, 2016", 13 pgs.
"U.S. Appl. No. 14/278,916, Non Final Office Action dated Dec. 9, 2015", 10 pgs.
"U.S. Appl. No. 14/278,916, Response filed May 9, 2016 to Final Office Action dated Dec. 9, 2015", 14 pgs.
"U.S. Appl. No. 14/722,701, Final Office Action dated Sep. 15, 2016", 12 pgs.
"U.S. Appl. No. 14/722,701, Non Final Office Action dated May 6, 2016", 18 pgs.
"U.S. Appl. No. 14/722,701, Response filed Aug. 3, 2016 to Non Final Office Action dated May 6, 2016", 15 pgs.
"U.S. Appl. No. 14/936,929, Preliminary Amendment filed Nov. 11, 2015", 7 pgs.
"European Application Serial No. 13715785.5, Decision to Grant dated Feb. 4, 2016", 2 pgs.
"European Application Serial No. 13715785.5, Office Action dated Sep. 7, 2015", 26 pgs.
"European Application Serial No. 13715785.5, Response filed May 27, 2015 to Communication pursuant to Rules 161(2) and 162 EPC dated Nov. 20, 2014", 22 pgs.

* cited by examiner

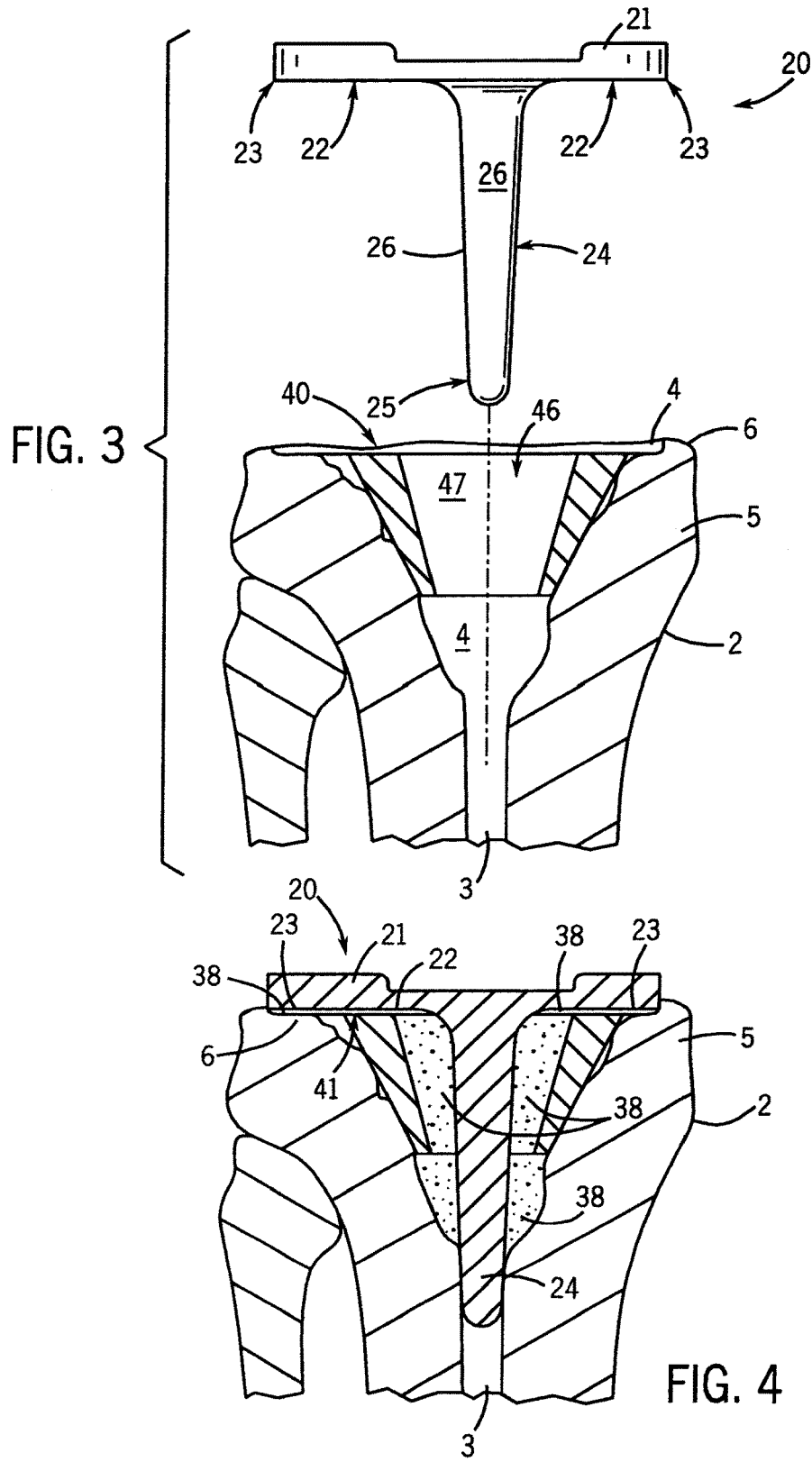

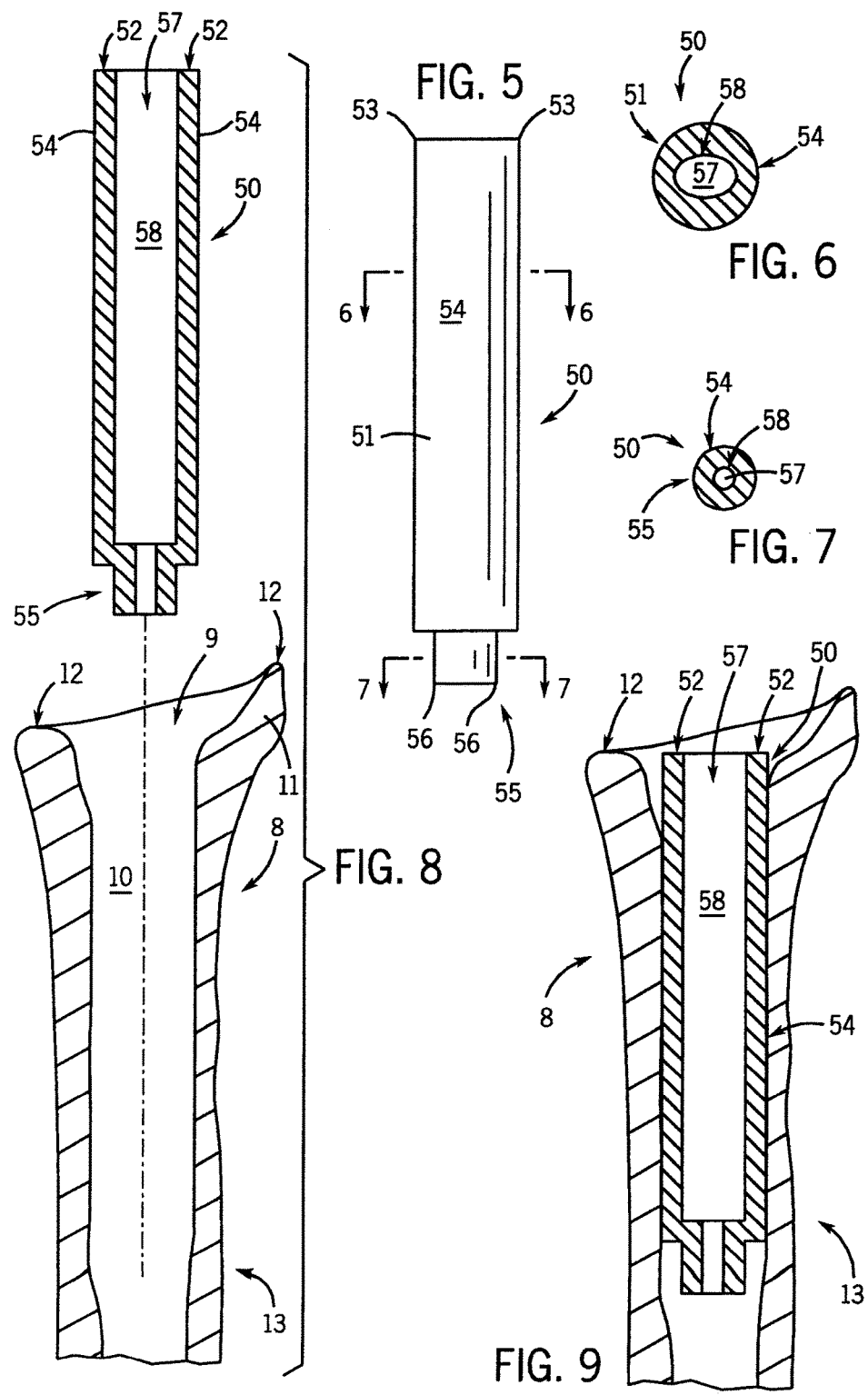

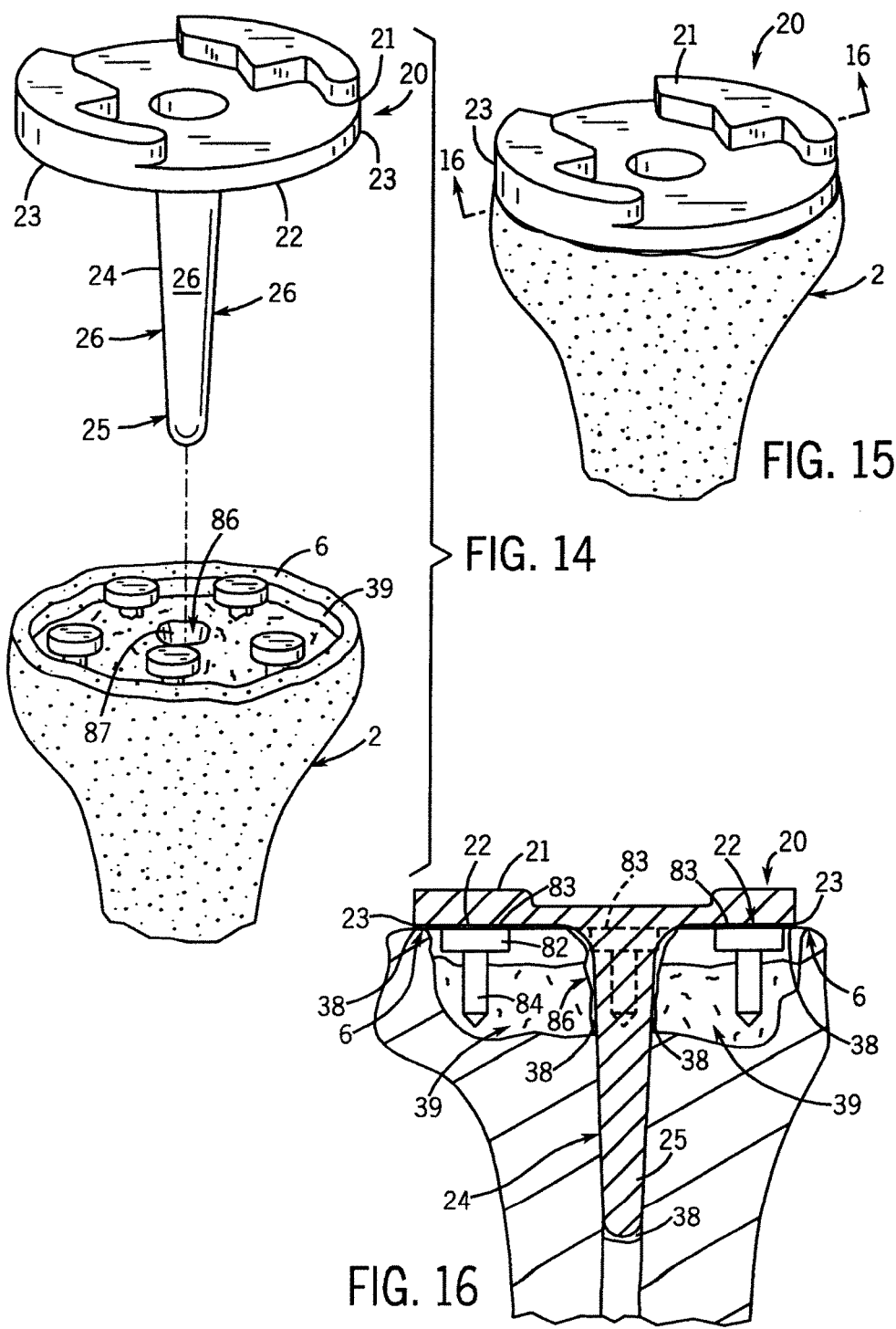

PROSTHETIC IMPLANT SUPPORT STRUCTURE

CROSS-REFERENCE TO RELATED APPLICATIONS

This is a continuation application of U.S. patent application Ser. No. 12/946,132, filed on Nov. 15, 2010, which is a continuation of U.S. patent application Ser. No. 11/560,276 filed Nov. 15, 2006, which is a divisional application of U.S. patent application Ser. No. 10/225,774 filed Aug. 22, 2002, which claims the benefit of U.S. Provisional Patent Application No. 60/315,148 filed Aug. 27, 2001, the disclosures of which are hereby incorporated by reference herein in their entireties.

STATEMENT REGARDING FEDERALLY SPONSORED RESEARCH

Not Applicable.

BACKGROUND OF THE INVENTION

1. Field of the Invention

This invention relates to prosthetic devices for implantation within a bone, and more particularly to support structures that are affixed to a bone and that support prosthetic implants.

2. Description of the Related Art

The replacement of joints, such as the shoulder, hip, knee, ankle and wrist, with prosthetic implants has become widespread. One problem commonly encountered by surgeons replacing joints is the loss of strong bone stock near the joint being replaced. Defects in a bone adjacent a joint, such as the hip or knee, can occur due to wear and arthritis of the joint, congenital deformity, and following the removal of a failed prosthetic implant. Defects can be of a cavitary contained type or segmental and uncontained. Because such bone defects are quite common, various methods have been proposed for minimizing the adverse effects of such bone defects on joint replacement procedures.

It is known to use bone graft to prepare a support surface for a prosthesis, either with or without the use of cement. A bone grafting procedure is often used where there is an appreciable loss of strong bone stock, as is often the case in revision surgery where a previously implanted prosthesis is replaced with a new prosthesis. The support surface prepared with bone graft may be made up entirely of bone graft to substantially surround a prosthesis, or the support surface may be made up of bone graft and the natural bone at the implantation site (for instance, where bone graft is used to fill a relatively small void in the natural bone where the bone is otherwise intact). Bone graft typically includes crushed bone (cancellous and cortical), or a combination of these and synthetic biocompatible materials. Bone graft of this type is intended to stimulate growth of healthy bone. Examples of bone graft materials and related materials can be found in U.S. Pat. Nos. 5,972,368, 5,788,976, 5,531,791, 5,510,396, 5,356,629, 4,789,663 and 4,678,470. Bone graft may be positioned in a bone cavity by various methods such as those described in U.S. Pat. Nos. 6,142,998, 6,013,080 and 5,910,172. The use of bone graft to prepare a support surface for a prosthesis does have certain disadvantages as bone graft may not be readily available in all areas and the devices used to deliver bone graft can be quite cumbersome.

In the presence of bone deficiency, stemmed components are also often used as a method to augment prosthesis fixation during complex primary or revision knee and hip arthroplasty. These stems may be cemented or uncemented; however, the most common method of fixation during revision knee arthroplasty is the use of an uncemented stem combined with cement fixation of the prosthesis in the metaphyseal region. However, due to the large variation of bone quality, interdigitation of bone cement into the metaphyseal region is often suboptimal such that cement fixation of the stem in the bone cavity is necessary. While cement fixation of the stem provides for improved prosthesis fixation, it does have disadvantages. For example, one recognized problem with the use of a cemented stem is that the transfer of stress from the implant to the bone is abnormal. Instead of a normal loading of the bone primarily at the end of the bone near the joint surface, the bone is loaded more distally where the stem of the implant is affixed to the bone. This results in the well known phenomenon called "stress shielding" in which the load (i.e., stress) bypasses or "unloads" the end of the joint surface portion of the bone.

In the presence of severe bone deficiency, the diaphyseal region of the bone is often deficient or absent and requires the use of bone graft or unique prosthetic designs to achieve adequate prosthesis fixation during complex primary or revision knee and hip arthroplasty. The use of large structural allografts to restore bone stock requires a sophisticated bone banking system and is associated with the potential transmission of viral or bacterial pathogens. Furthermore, the difficulties with sizing and bone graft preparation are cumbersome and inexact.

When the bone deficiency occurs at the end surface of a bone, prosthetic implant augmentation devices are also often used. Typically, these devices comprise an implant body and a spacer that is attached to the implant body to form a bearing surface on the implant. The implant is affixed to the bone with the bearing surface resting on the end of the bone, essentially acting as a replacement for lost bone. U.S. Pat. Nos. 5,480,445, 5,387,241, 5,152,797 and 5,019,103 show examples of such devices. While these types of implant augmentation devices provide one solution to the problems associated with the implantation of a prosthesis in the end surface of a bone with inadequate bone stock, these implant augmentation devices can only be used with specific implants available from selected implant manufacturers.

In the context of hip arthroplasty, oversized acetabular components and morselized bone grafts have been used to restore bone deficiencies, but larger defects have in the past been associated with a high failure rate despite efforts at reconstruction using large solid structural allografts or custom acetabular components. These devices gain support against the residual bone of the pelvis but often lack adequate bony support for long term mechanical durability.

Therefore, there is a need for alternative prosthetic implant support structures that do not rely on the use of large amounts of bone graft or cumbersome bone graft delivery devices. There is also a need for prosthetic implant support structures that can eliminate the need to cement the distal portion of the stem of an implant to the inner surface of a bone cavity. In addition, there is a need for prosthetic implant support structures that can be used with a wide variety of prosthetic implants obtained from any number of different implant manufacturers. Furthermore, there is a need for a prosthetic implant system that optimizes implant support on intact host bone with minimal removal of residual host bone and that encourages bone ingrowth and attachment over as large a surface area as possible.

SUMMARY OF THE INVENTION

The foregoing needs are met by a prosthetic system according to the invention that is implanted in a cavity in an end of a bone. The prosthetic system includes a prosthetic implant and a support structure secured to an inner surface of the cavity in the end of the bone. The support structure defines an axial channel that extends through the length of the support structure. The prosthetic implant is received in the channel of the support structure, and a portion of the prosthetic implant is secured to an inner surface of the channel of the support structure by an adhesive.

In one version of the invention, the support structure comprises a hollow sleeve having a sloped outer surface such that the length of a first perimeter of one end of the sleeve is greater than the length of a second perimeter at an opposite end of the sleeve. Such a support structure may have an approximately funnel shape. At the junction of the metaphysis and diaphysis of a bone such as the femur or tibia, the bone defect is often funnel shaped. Accordingly, a funnel shaped support structure in accordance with the invention can be impacted into the distal femur or proximal tibia so that the external geometry of the funnel shaped support structure is firmly wedged in the metaphyseal-diaphyseal junction of the bone. The internal portion of the funnel shaped support structure provides an access channel that allows passage of the stem extending from a traditional prosthesis of any prosthetic design or manufacturer. The stem of the prosthesis is cemented to the inner surface of the access channel using bone cement, and the stem extension beyond the funnel shaped support structure may be cemented or uncemented.

In another version of the invention, the support structure comprises a hollow porous cylindrical sleeve. The sleeve can be inserted into a large cavernous diaphyseal bone defect or can be used as a replacement for segmental or complete diaphyseal bone deficiency. The sleeve can be a number of different sizes and lengths so that a surgeon can pick the appropriate sized sleeve for the patient after intraoperative assessment and thereby avoid difficulties of size mismatch and bone graft contouring. The sleeve can accommodate any number of prosthetic designs and can achieve fixation to remaining host tissue by soft tissue or bone ingrowth. A stem of a prosthesis is fixed within the sleeve by use of bone cement, and the stem of the prosthesis beyond the sleeve may be cemented or uncemented.

In yet another version of the invention, the support structure comprises a pair of components arranged in spaced apart relationship thereby defining a channel between the pair of components. The support structure may be based on hemispherical shapes (such as a configuration approximating a quarter of a sphere) which are provided in a range of sizes for the creation of a prosthetic foundation for support of standard tibial, femoral, or acetabular components. While this support structure is particularly useful in the acetabulum and hip, the support structure is appropriate for all joints undergoing prosthetic replacement with a wide range of shapes and sizes necessary for management of defects in different locations. The support structure is compatible with a range of standard implant designs currently available from a variety of manufacturers. The interface between the pair of components and the prosthetic implant is cemented with bone cement. All surfaces against host bone may be uncemented and are available for bone ingrowth into porous materials used for the components. Optionally, morselized cancellous bone may be placed into fenestrations in the pair of components and supplemental screw fixation of the pair of components to bone may be used to encourage bone ingrowth and secure fixation to host bone over the long term.

In still another version of the invention, the support structure comprises a plurality of pedestals secured to the inner surface of the cavity of the bone. Each pedestal comprises a flat body section and a stem section extending substantially perpendicularly from the body section. The stem section of each pedestal is secured to the inner surface of the cavity of the bone, and the flat body sections of the pedestals are secured to a portion of a bearing surface of the prosthetic implant. The support structure may further comprise bone graft material surrounding the plurality of pedestals. In one form, the pedestals and the bone graft material are arranged in a circular arrangement whereby the channel that extends through the length of the support structure is circular. A stem of a prosthesis is fixed within the channel by use of bone cement, and the stem of the prosthesis beyond the channel may be cemented or uncemented.

It is therefore an advantage of the present invention to provide prosthetic implant support structures that do not rely on the use of large amounts of bone graft or cumbersome bone graft delivery devices.

It is another advantage of the present invention to provide prosthetic implant support structures that can eliminate the need to cement the distal portion of the stem of an implant to the inner surface of a bone cavity.

It is a further advantage of the present invention to provide prosthetic implant support structures that can be used with a wide variety of prosthetic implants obtained from any number of different implant manufacturers.

It is yet another advantage of the present invention to provide a prosthetic implant system that optimizes implant support on intact host bone with minimal removal of residual host bone and that encourages bone ingrowth and attachment over as large a surface area as possible.

These and other features, aspects, and advantages of the present invention will become better understood upon consideration of the following detailed description, drawings, and appended claims.

BRIEF DESCRIPTION OF THE DRAWINGS

FIG. 3 is a side view of a prosthetic implant being placed in the prosthetic implant support structure in the tibia as shown in FIG. 2;

FIG. 4 is a cross-sectional view of the prosthetic implant as placed in the prosthetic support structure in the tibia as shown in FIG. 3;

FIG. 5 is a side view of another embodiment of a prosthetic implant support structure according to the invention;

FIG. 6 is a cross-sectional view of the prosthetic implant support structure of FIG. 5 taken along line 6-6 of FIG. 5;

FIG. 7 is another cross-sectional view of the prosthetic implant support structure of FIG. 5 taken along line 7-7 of FIG. 5;

FIG. 8 is cross-sectional view of the prosthetic implant support structure of FIG. 5 being placed in a femur;

FIG. 9 is a cross-sectional view of the prosthetic support structure of FIG. 5 as placed in the femur as shown in FIG. 8;

FIG. 14 is an exploded perspective view of a prosthetic implant being placed in the prosthetic support structure of FIG. 12 as placed in the tibia as shown in FIG. 13;

FIG. 15 is a perspective view of a prosthetic implant placed in the prosthetic support structure of FIG. 12 as placed in the tibia as shown in FIG. 13;

FIG. 16 is cross-sectional view of a prosthetic implant placed in the prosthetic support structure as placed in the tibia taken along line 16-16 of FIG. 15;

Figure 1:
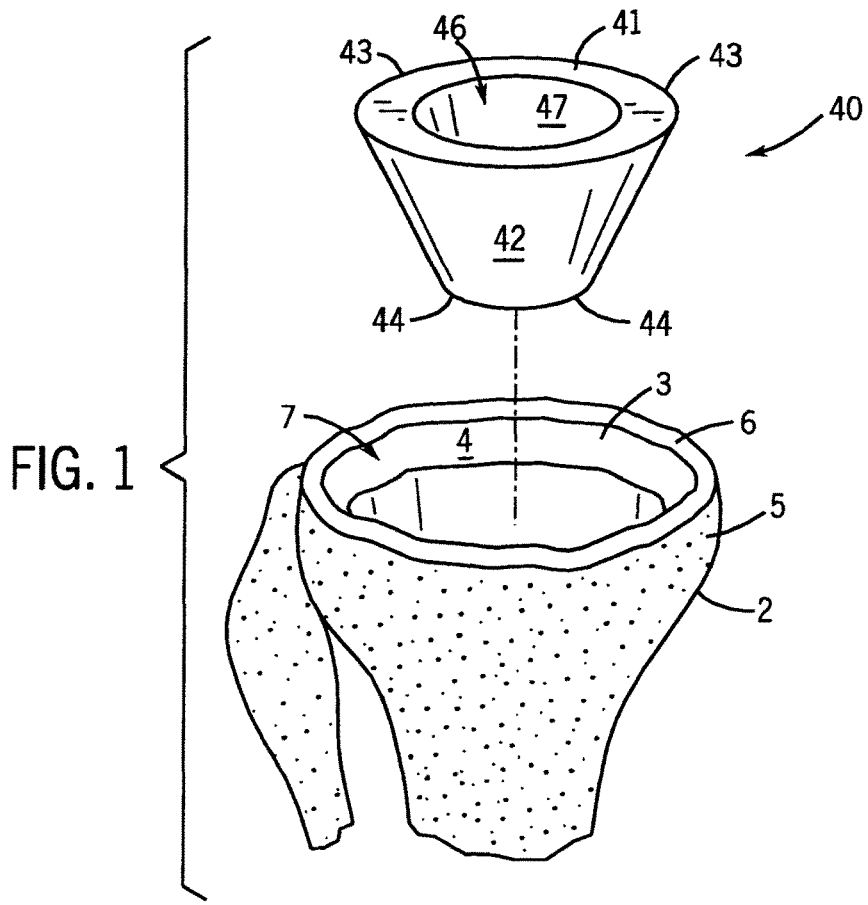
FIG. 1 is an exploded perspective view of one embodiment of a prosthetic implant support structure according to the invention being placed in a tibia.

It should be understood that the drawings are not necessarily to scale and that the embodiments are sometimes illustrated by diagrammatic representations and fragmentary views. In certain instances, details which are not necessary for an understanding of the present invention or which render other details difficult to perceive may have been omitted. It should be understood, of course, that the invention is not necessarily limited to the specific embodiments illustrated herein.

Like reference numerals will be used to refer to like or similar parts from Figure to Figure in the following description of the drawings.

DETAILED DESCRIPTION OF THE INVENTION

The present invention is directed to a prosthetic system that includes a prosthetic implant and a support structure secured to an inner surface of the cavity in the end of the bone. The prosthetic system and the methods for its use are illustrated and described herein with reference to the replacement of a hip joint or a knee joint. However, it should be understood that the methods and prosthetic systems according to the invention can be used in the repair of any bone or in connection with the implantation of prosthetic devices at or in any bone in the body, adjacent to or remote from any joint, including without limitation the hip, knee and spinal joints. Further, the methods and prosthetic systems according to the invention can be used in primary surgery, in which a prosthesis is being used to reconstruct a joint for the first time, as well as in revision surgery, in which a previously-implanted prosthesis is being replaced with another prosthesis. Press fit, cement or other fixation techniques can be employed in conjunction with the methods and prosthetic systems according to the invention.

Looking first at FIGS. 1 to 4, there is shown a prosthetic system that includes a tibial implant 20 and a funnel shaped sleeve 40 that is secured to the inner surface 4 of the medullary canal (cavity) 3 of the end portion 5 of a tibia 2. The tibial implant 20, which is best shown in FIG. 3, has a body portion 21 and a stem 24 which extends outward from the body portion 21. The body portion 21 includes a bearing surface 22 that is typically affixed to the end surface 6 of the end portion 5 of the tibia. The outer limits of the bearing surface 22 define a perimeter 23. The stem 24 of the tibial implant 20 has a distal portion 25 and an outer surface 26. The tibial implant 20 is of conventional design and articulates with a femoral knee prosthesis (not shown) as is well known in the art.

Figure 2:
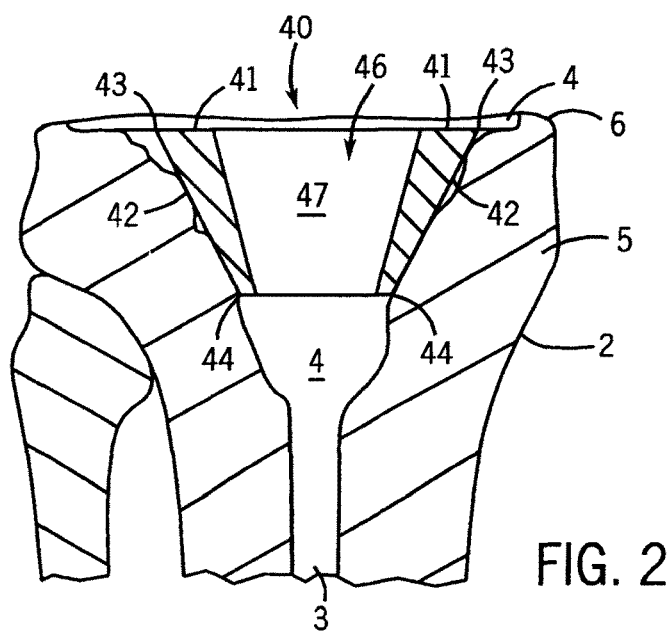
FIG. 2 is a cross-sectional view of the prosthetic implant support structure of FIG. 1 as placed in a tibia.

Referring to FIG. 1, there is shown the tibia 2 and the funnel shaped sleeve 40 that supports the tibial implant 20 as will be described below. From FIG. 1, it can be seen that at the junction of the metaphysis and diaphysis of the tibia 2, there is a funnel shaped bone defect 7 which can be fashioned to provide a large surface area of bone. The funnel shaped sleeve 40 is impacted into the end portion 5 of the tibia 2 so that the external geometry of the funnel shaped sleeve 40 is firmly wedged into the metaphyseal-diaphyseal junction as shown in FIG. 2.

The funnel shaped sleeve 40 defines an axial access channel 46 that extends through the length of the funnel shaped sleeve 40. The funnel shaped sleeve 40 has a top end surface 41, an outer surface 42, and an inner surface 47 of the access channel 46. In the version of the funnel shaped sleeve 40 shown, the outer surface 42 of the funnel shaped sleeve 40 is sloped such that the length of a top end perimeter 43 of the funnel shaped sleeve 40 is greater than the length of a bottom end perimeter 44 at an opposite end of the funnel shaped sleeve 40. The inner surface 47 of the access channel 46 may be similarly sloped if desired. The funnel shaped sleeve 40 may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, the funnel shaped sleeve 40 is formed from a metal alloy.

The outer surface 42 of the funnel shaped sleeve 40 may be provided with a metallic texture coating which provides a textured surface so as to attain the desired fixation (by way of tissue ingrowth) between the funnel shaped sleeve 40 and the inner surface 4 of the medullary canal (cavity) 3 of the end portion 5 of the tibia 2 within which the funnel shaped sleeve 40 is implanted. The inner surface 47 of the access channel 46 of the funnel shaped sleeve 40 has a rough or corrugated surface finish to facilitate the interdigitation of bone cement. Likewise, the top end surface 41 of the funnel shaped sleeve 40 has a rough or corrugated surface finish to facilitate the interdigitation of bone cement. The funnel shaped sleeve 40 may have a variety of shapes and sizes, which vary by height, width and depth. A surgeon can use conventional measurement tools to select the height, width and depth of the funnel shaped sleeve 40.

The prosthetic system shown in FIGS. 1 to 4 may be implanted in a bone as follows. First, the end portion 5 of the tibia 2 is inspected and tools (such as a reamer) may be used to clean material out of the medullary canal (cavity) 3 or the bone defect 7 (if any). Once the medullary canal (cavity) 3 and the bone defect 7 have been prepared, the funnel shaped sleeve 40 is impacted into the end portion 5 of the tibia 2 so that the external geometry of the funnel shaped sleeve 40 is firmly wedged into the tibia 2. If desired, conventional bone cement such as an acrylic cement (e.g., polymethyl methacrylate) may be used to secure the outer surface 42 of the funnel shaped sleeve 40 to the inner surface 4 of the medullary canal (cavity) 3 of the end portion 5 of a tibia 2. Next, the stem 24 of the tibial implant 20 is moved into the access channel 46 of the funnel shaped sleeve 40. As shown in FIG. 4, at least a portion of the outer surface 26 of the stem 24 of the tibial implant 20 is secured to the inner surface 47 of the access channel 46 of the funnel shaped sleeve 40 with a suitable adhesive such as bone cement 38 (e.g., polymethyl methacrylate). Optionally, the distal portion 25 of the tibial implant 20 (which extends beyond the length of the funnel shaped sleeve 40) may be secured to the inner surface 4 of the medullary canal (cavity) 3 of the tibia 2 with a suitable adhesive such as bone cement 38 (e.g., polymethyl methacrylate).

Looking at FIG. 4 (which shows the tibial implant 20 and the funnel shaped sleeve 40 implanted in the tibia 2), several aspects of the invention can be described. For example, it can be seen that a portion of the bearing surface 22 of the tibial implant 20 is secured by cement 38 to the top end surface 41 of the funnel shaped sleeve 40 adjacent the end portion 5 of the tibia 2. The top end surface 41 of the funnel shaped sleeve 40 provides a rough or corrugated surface finish to facilitate the interdigitation of bone cement and provides an attachment surface for the tibial implant 20 where bone stock has been lost. Also, the region near the perimeter 23 of the bearing surface 22 of the tibial implant 20 is secured by cement 38 to the end surface 6 of the end portion 5 of the tibia 2. This provides for additional support for the tibial implant 20. The simultaneous attachment of the bearing surface 22 of the tibial implant 20 to the top end surface 41 of the funnel shaped sleeve 40 and to the end surface 6 of the end portion 5 of the tibia 2 is possible because the funnel shaped sleeve 40 is positioned in the cavity 3 of the tibia 2 such that the funnel shaped sleeve 40 does not extend beyond a plane defined by the end surface 6 of the end portion 5 of the tibia 2.

Because the funnel shaped sleeve 40 is not an integral component of the tibial implant 20, the funnel shaped sleeve 40 can be used with any stemmed prosthesis regardless of manufacturer or prosthetic design. Further, it should be noted that the example given in FIGS. 1 to 4 relates to use of the funnel shaped sleeve 40 in the proximal tibia; however, another common site where the funnel shaped sleeve 40 would be frequently used is the distal femur. Still other anatomic sites would include any joint that undergoes prosthetic arthroplasty when there is a significant metaphyseal bone deficiency.

In the presence of severe bone deficiency, the diaphyseal region of a bone is often deficient or absent and often requires the use of bone graft or unique prosthetic designs to achieve adequate prosthesis fixation during complex primary or revision knee and hip arthroplasty. As detailed above, the use of large structural allografts to restore bone stock requires a sophisticated bone banking system and is associated with the potential transmission of viral or bacterial pathogens. Furthermore, the difficulties with sizing and bone graft preparation are cumbersome and inexact. The advantages of minimizing disease transmission by minimizing use of allograft material and reduced operative times can be achieved with another prosthetic system according to the invention as shown in FIGS. 5 to 11. The prosthetic system allows for the insertion of a cylindrical porous sleeve into a large cavernous diaphyseal bone defect and also allows for the replacement of a segmental or complete diaphyseal bone deficiency.

Figures 10, 11:
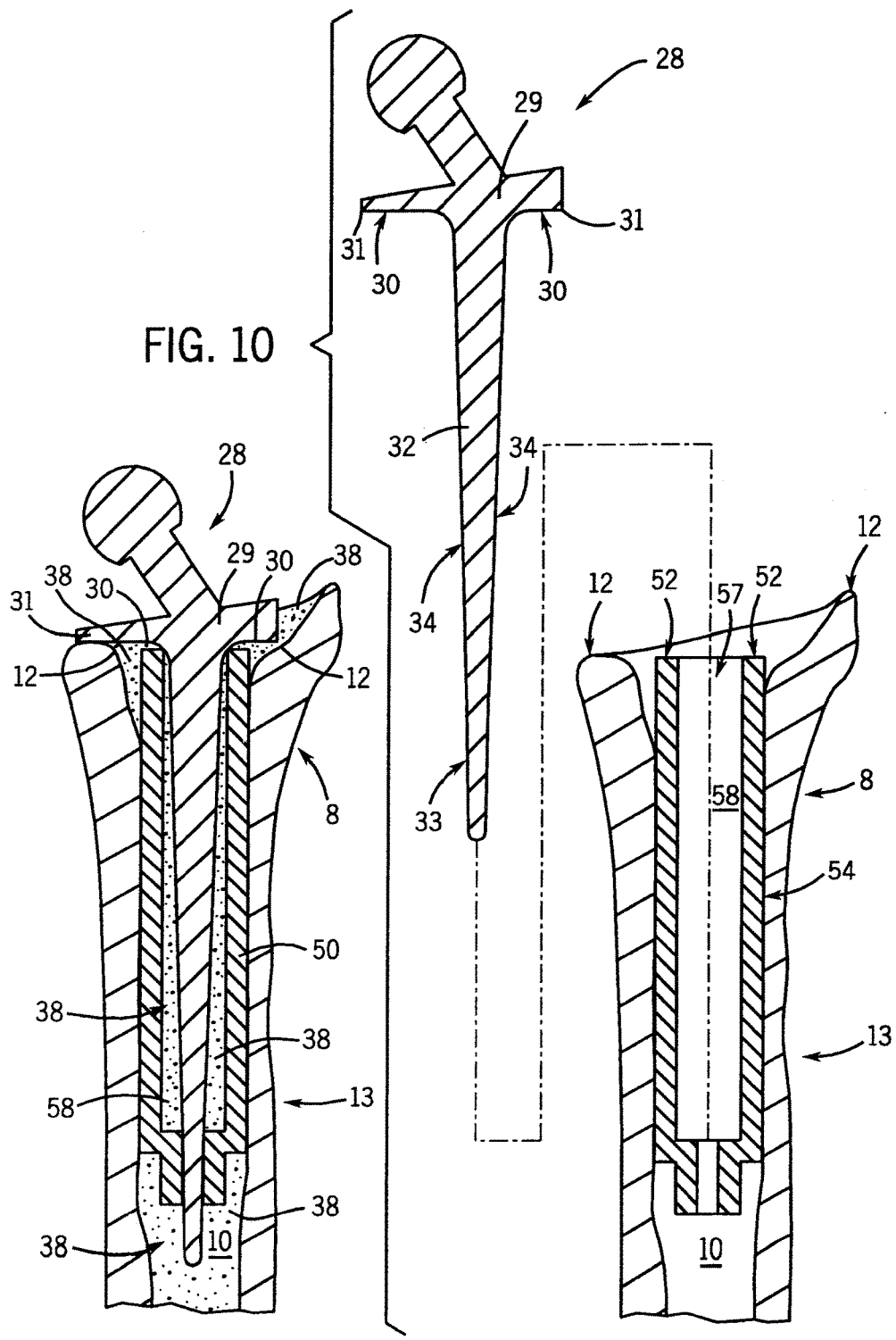
FIG. 10 is a cross-sectional view of a prosthetic implant being placed in the prosthetic support structure of FIG. 5 as placed in the femur as shown in FIG. 9.
FIG. 11 is a cross-sectional view of a prosthetic implant placed in the prosthetic support structure of FIG. 5 as placed in the femur as shown in FIG. 9.

Referring now to FIGS. 5 to 11, there is shown a prosthetic system that includes a femoral implant 28 and a cylindrically shaped sleeve 50 that is secured to the inner surface 10 of the medullary canal (cavity) 9 of a femur 8. The femoral implant 28, which is best shown in FIG. 10, has a body portion 29 and a stem 32 which extends outward from the body portion 29. The body portion 29 includes a bearing surface 30 that is typically affixed to the end surface 12 of the end portion 11 of the femur 8. The outer limits of the bearing surface 30 define a perimeter 31. The stem 32 of the femoral implant 28 has a distal portion 33 and an outer surface 34. The femoral implant 28 is of conventional design and is secured for movement within an acetabular cup (not shown) as is well known in the hip replacement art.

Referring to FIG. 8, there is shown the femur 8 and the cylindrical sleeve 50 that supports the femoral implant 28 as will be described below. From FIG. 8, it can be seen that at the diaphyseal region 13 of the femur 8, there is a bone defect. The cylindrical sleeve 50 is impacted into the cavity 9 of the femur 8 so that the external geometry of the cylindrical sleeve 50 is firmly wedged into the diaphyseal region 13 of the femur as shown in FIG. 9.

The cylindrical sleeve 50 defines an axial access channel 57 that extends through the length of the cylindrical sleeve 50. The cylindrical sleeve 50 has a top end surface 52, an outer surface 54, and an inner surface 58 of the access channel 57. The cylindrical sleeve 50 has a cylindrical upper section 51 having a first outside diameter and a cylindrical lower section 55 having a second outside diameter less than the first outside diameter. The access channel 57 may be cylindrical or optionally, the access channel 57 may be configured to accept various implant stem designs. For example, it can be seen from FIG. 6 that the access channel 57 in the upper section 51 of the cylindrical sleeve 50 has an approximately oval cross-section and from FIG. 7 that the access channel 57 in the lower section 55 of the cylindrical sleeve 50 has an approximately circular cross-section. The cylindrical sleeve 50 may be formed from a porous metal alloy such as titanium alloys (e.g., titanium-6-aluminum-4-vanadium), cobalt-chromium alloys, stainless steel alloys and tantalum alloys; nonresorbable porous ceramics such as aluminum oxide and zirconia; nonresorbable porous polymeric materials such as polyethylene; or porous composite materials such as carbon fiber-reinforced polymers (e.g., polysulfone). Preferably, the cylindrical sleeve 50 is formed from a porous metal alloy.

The outer surface 54 of the cylindrical sleeve 50 may also be provided with a metallic texture coating which provides a textured surface so as to attain the desired fixation (by way of tissue ingrowth) between the cylindrical sleeve 50 and the inner surface 10 of the medullary canal (cavity) 9 of the femur 8 within which the cylindrical sleeve 50 is implanted. The inner surface 58 of the access channel 57 of the cylindrical sleeve 50 has a rough or corrugated surface finish to facilitate the interdigitation of bone cement. Likewise, the top end surface 52 of the cylindrical sleeve 50 has a rough or corrugated surface finish to facilitate the interdigitation of bone cement. The cylindrical sleeve 50 may comprise any number of different sizes and lengths so that a surgeon is able to pick the appropriate sized sleeve for the patient after intraoperative assessment and thereby avoid difficulties of size mismatch and bone graft contouring. A surgeon can use conventional measurement tools to select the length and width of the cylindrical sleeve 50.

The prosthetic system shown in FIGS. 5 to 11 may be implanted in a bone as follows. First, the cavity 9 of the femur 8 is inspected and tools (such as a reamer) may be used to clean material out of the medullary canal (cavity) 9 or the bone defect (if any). Once the medullary canal (cavity) 9 and the bone defect have been prepared, the cylindrical sleeve 50 is impacted into the femur 2 so that the external geometry of the cylindrical sleeve 50 is firmly wedged into the femur 8. If desired, conventional bone cement such as an acrylic cement (e.g., polymethyl methacrylate) may be used to secure the outer surface 54 of the cylindrical sleeve 50 to the inner surface 10 of the medullary canal (cavity) 9 of the femur 8. Next, the stem 32 of the femoral implant 28 is moved into the access channel 57 of the cylindrical sleeve 50. As shown in FIG. 11, at least a portion of the outer surface 34 of the stem 32 of the femoral implant 28 is secured to the inner surface 58 of the access channel 57 of the cylindrical sleeve 50 with a suitable adhesive such as bone cement 38 (e.g., polymethyl methacrylate). Implant fixation within the sleeve 50 is achieved by cement interdigitation into the rough or corrugated surface finish of the inner surface 58 of the access channel 57 of the cylindrical sleeve 50 or into the porous structure of the sleeve. Optionally, the distal portion 33 of the femoral implant 28 (which extends beyond the length of the cylindrical sleeve 50) may be secured to the inner surface 10 of the medullary canal (cavity) 9 of the femur 8 with a suitable adhesive such as bone cement 38 (e.g., polymethyl methacrylate).

Looking at FIG. 11 (which shows the femoral implant 28 and the cylindrical sleeve 50 implanted in the femur 8), several aspects of the invention can be described. For example, it can be seen that a portion of the bearing surface 30 of the femoral implant 28 is secured by cement 38 to the top end surface 12 of the cylindrical sleeve 50 adjacent the end portion 11 of the femur 8. The top end surface 52 of the cylindrical sleeve 50 provides a rough or corrugated surface finish to facilitate the interdigitation of bone cement and provides an attachment surface for the femoral implant 28 where bone stock has been lost. Also, the region near the perimeter 31 of the bearing surface 30 of the femoral implant 28 is secured by cement 38 to the end surface 12 of the end portion 11 of the femur 8. This provides for additional support for the femoral implant 28. The simultaneous attachment of the bearing surface 30 of the femoral implant 28 to the top end surface 52 of the cylindrical sleeve 50 and to the end surface 12 of the end portion 11 of the femur 8 is possible because the cylindrical sleeve 50 is positioned in the cavity 9 of the femur 8 such that the cylindrical sleeve 50 does not extend beyond a plane defined by the end surface 12 of the end portion 11 of the femur 8.

Because the cylindrical sleeve 50 is not an integral component of the femoral implant 28, the cylindrical sleeve 50 can be used with any stemmed prosthesis regardless of manufacturer or prosthetic design. The sleeve can accommodate any number of prosthetic designs and achieves fixation to remaining host tissue by soft tissue or bone ingrowth. Further, it should be noted that the example given in FIGS. 5 to 11 relates to use of the cylindrical sleeve 50 in the proximal femur; however, another common site where the cylindrical sleeve 50 would be frequently used is the proximal tibia. Still other anatomic sites would include any joint that undergoes prosthetic arthroplasty when there is a significant diaphyseal bone deficiency.

Turning now to FIGS. 12 to 16, there is shown a yet another prosthetic system according to the invention that includes a tibial implant 20 and a periprosthetic support structure, indicated generally at 80, that is secured to the inner surface 4 of the medullary canal (cavity) 3 of the end portion 5 of a tibia 2. The tibial implant 20, which is shown in FIGS. 14 to 16, is identical to the tibial implant 20 that was described above with reference to FIGS. 1 to 4 and therefore will not be described again.

Figure 12:
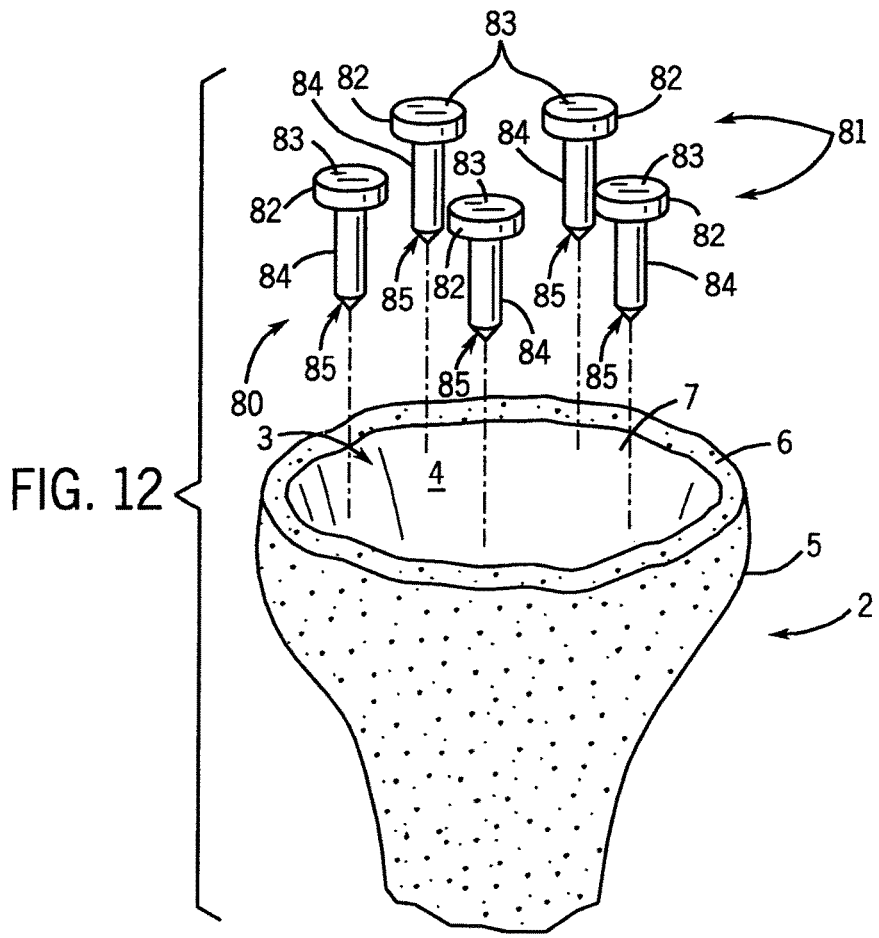
FIG. 12 is an exploded perspective view of yet another embodiment of a prosthetic implant support structure according to the invention being placed in a tibia.
Figure 13:
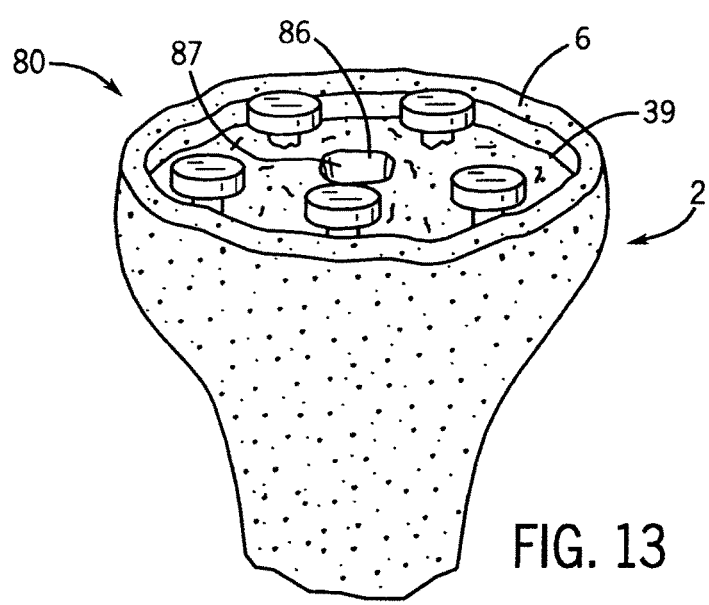
FIG. 13 is a perspective view of the prosthetic implant support structure of FIG. 12 as placed in a tibia.

Referring to FIG. 12, there is shown the tibia 2 and the periprosthetic support structure 80 that supports the tibial implant 20 as will be described below. From FIG. 12, it can be seen that at the junction of the metaphysis and diaphysis of the tibia 2, there is a funnel shaped bone defect 7 which can be fashioned to provide a large surface area of bone. The components of the periprosthetic support structure 80 are impacted into the end portion 5 of the tibia 2 so that the components of the periprosthetic support structure 80 are firmly wedged into the metaphyseal-diaphyseal junction as shown in FIG. 13.

The periprosthetic support structure 80 comprises a plurality of pedestals 81 that are impacted into or cemented to the inner surface 4 of the medullary canal (cavity) 3 of the end portion 5 of a tibia 2. Each pedestal 81 includes a flat disk shaped body section 82 having a top surface 83 and a stem section 84 extending substantially perpendicularly from the body section 82. The stem section 84 optionally includes a pointed end section 85 that facilitates impaction into the inner surface 4 of the medullary canal (cavity) 3 of the end portion 5 of a tibia 2. Each pedestal 81 may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, each pedestal 81 is formed from a metal alloy. The outer surfaces of each pedestal 81 (including the top surface 83) may be provided with a rough or corrugated surface finish to facilitate the interdigitation of bone cement. The body section 82 of each pedestal 80 may have a variety of shapes and sizes as long as there exists a generally flat portion on part of the top surface. The stem section 84 of each pedestal 81 may also have various lengths and widths. A surgeon can use conventional measurement tools to select the dimensions of each pedestal 81.

The pedestals 81 may be implanted in a bone as follows to form the periprosthetic support structure 80. First, the end portion 5 of the tibia 2 is inspected and tools (such as a reamer) may be used to clean material out of the medullary canal (cavity) 3 or the bone defect 7 (if any). Once the medullary canal (cavity) 3 and the bone defect 7 have been prepared, the stem section 84 of each pedestal 81 is impacted into or cemented onto the end portion 5 of the tibia 2 to form the periprosthetic support structure 80. The pedestals 81 may be arranged in any configuration; however, it is preferred that the pedestals 81 are arranged in the circular arrangement shown in FIGS. 13 and 14. The circular arrangement of the pedestals 81 creates an access channel that extends through the length of the periprosthetic support structure 80. Optionally, the periprosthetic support structure 80 may include bone graft material 39 that is placed around the pedestals 81 to form an access channel 86 having an inner surface 87 as shown in FIGS. 13 and 14. The bone graft material 39 may selected from known bone graft materials and may include crushed bone (cancellous and cortical), or a combination of these and synthetic biocompatible materials. As used herein, "bone graft" shall mean materials made up entirely of natural materials, entirely of synthetic biocompatible materials, or any combination of these materials.

After the periprosthetic support structure 80 is formed in a bone, the stem 24 of the tibial implant 20 may be moved into the access channel 86 of the periprosthetic support structure 80. As shown in FIG. 16, at least a portion of the outer surface 26 of the stem 24 of the tibial implant 20 is secured to the inner surface 87 of the access channel 86 of the periprosthetic support structure 80 with a suitable adhesive such as bone cement 38 (e.g., polymethyl methacrylate). Optionally, the distal portion 25 of the tibial implant 20 (which extends beyond the length of the periprosthetic support structure 80) may be secured to the inner surface 4 of the medullary canal (cavity) 3 of the tibia 2 with a suitable adhesive such as bone cement 38 (e.g., polymethyl methacrylate).

Looking at FIGS. 15 and 16 (which show the tibial implant 20 and the periprosthetic support structure 80 implanted in the tibia 2), several aspects of the invention can be described. For example, it can be seen that a portion of the bearing surface 22 of the tibial implant 20 is secured by cement 38 to the top surface 83 of each pedestal 81 of the periprosthetic support structure 80 adjacent the end portion 5 of the tibia 2. The top end surface 83 of each pedestal 81 of the periprosthetic support structure 80 provides a rough or corrugated surface finish to facilitate the interdigitation of bone cement and provides an attachment surface for the tibial implant 20 where bone stock has been lost. Also, the region near the perimeter 23 of the bearing surface 22 of the tibial implant 20 is secured by cement 38 to the end surface 6 of the end portion 5 of the tibia 2. This provides for additional support for the tibial implant 20. The simultaneous attachment of the bearing surface 22 of the tibial implant 20 to the top end surface 83 of each pedestal 81 of the periprosthetic support structure 80 and to the end surface 6 of the end portion 5 of the tibia 2 is possible because the periprosthetic support structure 80 is positioned in the cavity 3 of the tibia 2 such that the periprosthetic support structure 80 does not extend beyond a plane defined by the end surface 6 of the end portion 5 of the tibia 2.

Because the periprosthetic support structure 80 is not an integral component of the tibial implant 20, the periprosthetic support structure 80 can be used with any stemmed prosthesis regardless of manufacturer or prosthetic design. Further, it should be noted that the example given in FIGS. 12 to 16 relates to use of the periprosthetic support structure 80 in the proximal tibia; however, another common site where the periprosthetic support structure 80 would be frequently used is the distal femur. Still other anatomic sites would include any joint that undergoes prosthetic arthroplasty when there is a significant metaphyseal bone deficiency.

Figure 17:
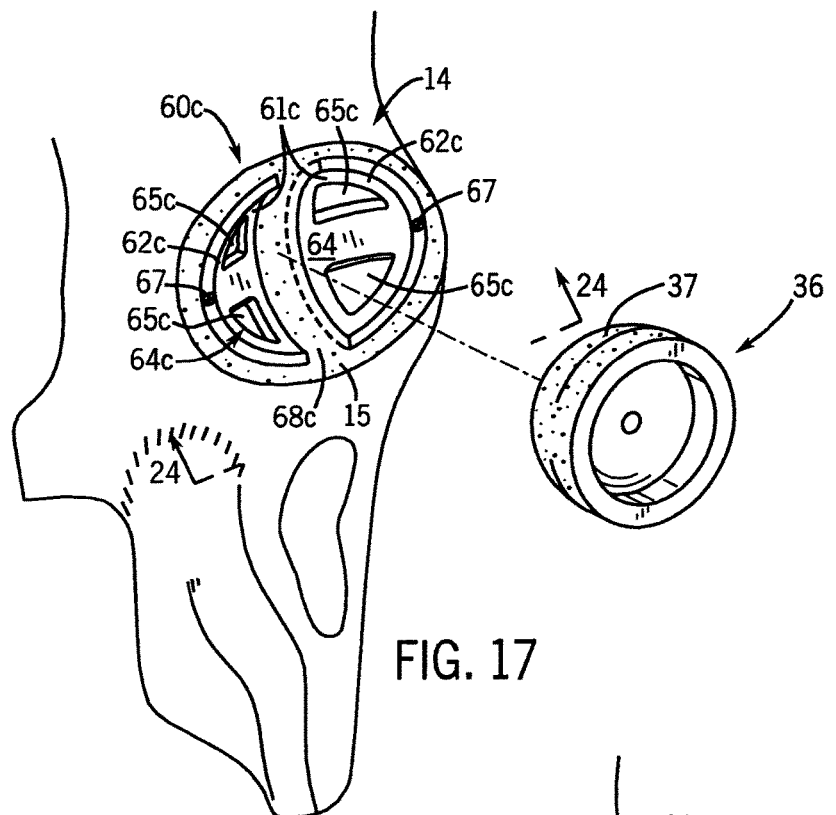
FIG. 17 is an exploded perspective view of an acetabular cup of a hip prosthesis being placed in still another embodiment of a prosthetic implant support structure according to the invention secured in the acetabular cavity of a hip.
Figure 24:
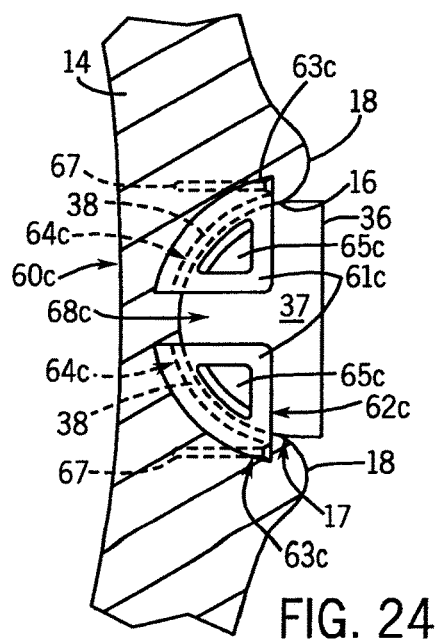
FIG. 24 is a cross-sectional view of an acetabular cup of a hip prosthesis placed in the prosthetic implant support structure of FIG. 17 taken along line 24-24 of FIG. 17.

Referring now to FIGS. 17 and 24, there is shown another prosthetic system according to the invention that includes an acetabular cup implant 36 having an outer surface 37 and a periprosthetic support structure, indicated generally at 60c, that is secured to the inner surface 16 of the acetabular cavity 15 of a hip bone 14. The periprosthetic support structure 60c comprises two support components 61c having a configuration approximating a quarter of a sphere. The support components 61c of the periprosthetic support structure 60c are impacted, screwed or cemented into the inner surface 16 of the acetabular cavity 15 of a hip bone 14 in a spaced apart relationship.

Each support component 61c may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, each support component 61c is formed from a metal alloy.

The outer surface 63c of each support component 61c may also be provided with a metallic texture coating which provides a textured surface so as to attain the desired fixation (by way of tissue ingrowth) between each support component 61c and the inner surface 16 of the acetabular cavity 15 of a hip bone 14 within which each support component 61c is implanted. The inner surface 64c of each support component 61c has a rough or corrugated surface finish to facilitate the interdigitation of bone cement. Likewise, the top end surface 62c of each support component 61c has a rough or corrugated surface finish to facilitate the interdigitation of bone cement. Each support component 61c also has fenestrations 65c which can be filled with bone graft material (e.g., morselized cancellous bone).

Each support component 61c may comprise any number of different heights, widths and depths so that a surgeon is able to pick the appropriate sized support component for the patient after intraoperative assessment and thereby avoid difficulties of size mismatch and bone graft contouring. A surgeon can use conventional measurement tools to select the size of each support component 61c. The size, position and orientation of each support component 61c and the use of supplemental screw fixation for each support component 61c is dependent on the size and location of the defects in the host bone as well as the quality of the bone that remains.

The support components 61c may be implanted in a bone as follows to form the periprosthetic support structure 60c. First, the acetabular cavity 15 of the hip bone 14 is inspected and tools (such as a reamer) may be used to clean material out of the acetabular cavity 15. Once the acetabular cavity 15 has been prepared, each support component 61c is impacted into or cemented onto the end portion 17 of the acetabular cavity 15 of the hip bone 14 in spaced apart relationship to form the periprosthetic support structure 60c. Preferably, each support component 61c is not cemented to the hip bone and therefore is available for bone ingrowth into the textured outer surface 63c of the support component 61c. The support components 61c shown in FIGS. 17 and 24 are also screwed into the hip bone 14 using screws 67 (shown in phantom in FIG. 24). The support components 61c may be arranged in any configuration that creates an access channel 68c that extends through the length of the periprosthetic support structure 60c. Preferably, the support components 61c are arranged to form a substantially hemispherical support structure. It can be seen that placement of the support components 61c precedes placement of any prosthetic joint components.

After the periprosthetic support structure 60c is constructed in a bone, the acetabular cup implant 36 may be placed into the access channel 68c of the periprosthetic support structure 60c. Placement can occur either during the same operative procedure as support component 61c placement or can be performed later once bone union to the support components 61c has occurred. In either instance, the acetabular cup implant 36 would be placed only after the acetabulum had been reconstructed using the support structure 60c. As shown in FIG. 24, at least a portion of the outer surface 37 of the acetabular cup implant 36 is secured to the inner surface 64c (shown in phantom) of the access channel 68c of the periprosthetic support structure 60c with a suitable adhesive such as bone cement 38 (e.g., polymethyl methacrylate). It can be seen that the periprosthetic support structure 60c does not extend beyond a plane defined by the end surface 18 of the end portion 17 of the hip bone 14.

Because the periprosthetic support structure 60c is not an integral component of the acetabular cup implant 36, the periprosthetic support structure 60c can be used with any acetabular cup implant 36 regardless of manufacturer or prosthetic design. Further, it should be noted that the example given in FIGS. 17 and 24 relates to use of the periprosthetic support structure 60c in the acetabular cavity of a hip bone; however, other common sites where the periprosthetic support structure 60c would be frequently used include the tibia and femur. Still other anatomic sites would include any joint that undergoes prosthetic arthroplasty when there is a significant metaphyseal bone deficiency.

Figure 18:
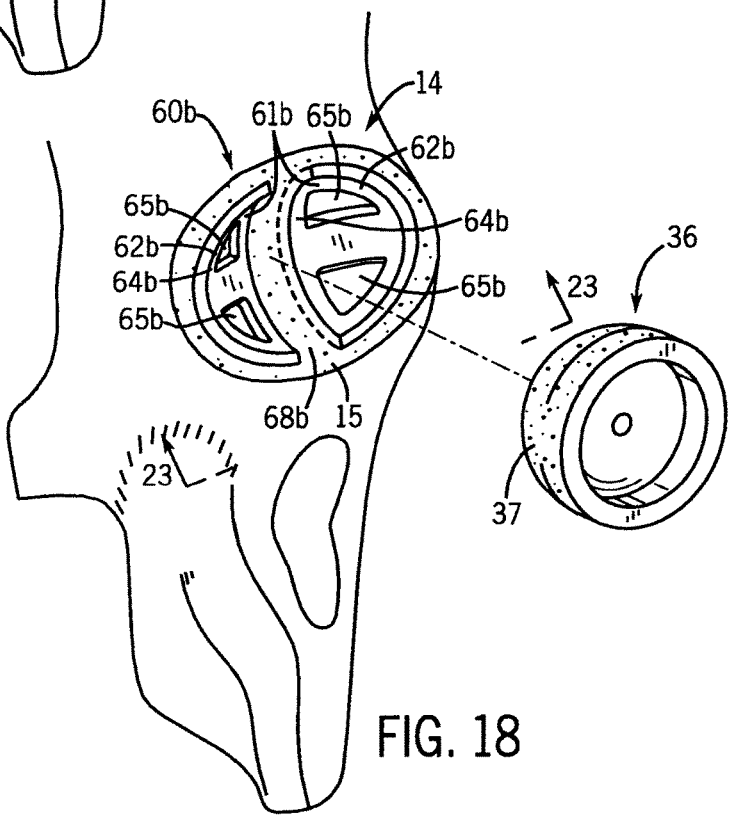
FIG. 18 is an exploded perspective view of an acetabular cup of a hip prosthesis being placed in a further embodiment of a prosthetic implant support structure according to the invention secured in the acetabular cavity of a hip.
Figure 23:
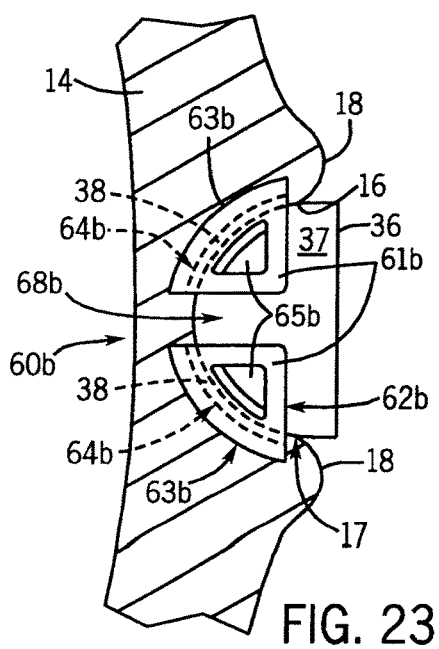
FIG. 23 is a cross-sectional view of an acetabular cup of a hip prosthesis placed in the prosthetic implant support structure of FIG. 18 taken along line 23-23 of FIG. 18.

Referring now to FIGS. 18 and 23, there is shown yet another prosthetic system according to the invention that includes an acetabular cup implant 36 having an outer surface 37 and a periprosthetic support structure, indicated generally at 60b, that is secured to the inner surface 16 of the acetabular cavity 15 of a hip bone 14. The periprosthetic support structure 60b comprises two support components 61b having a configuration approximating a quarter of a sphere. The support components 61b of the periprosthetic support structure 60b are impacted and/or cemented into the inner surface 16 of the acetabular cavity 15 of a hip bone 14 in a spaced apart relationship.

Each support component 61b may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, each support component 61b is formed from a metal alloy.

The outer surface 63b of each support component 61b may also be provided with a metallic texture coating which provides a textured surface so as to attain the desired fixation (by way of tissue ingrowth) between each support component 61b and the inner surface 16 of the acetabular cavity 15 of a hip bone 14 within which each support component 61b is implanted. The inner surface 64b of each support component 61b has a rough or corrugated surface finish to facilitate the interdigitation of bone cement. Likewise, the top end surface 62b of each support component 61b has a rough or corrugated surface finish to facilitate the interdigitation of bone cement. Each support component 61b also has fenestrations 65b which can be filled with bone graft material (e.g., morselized cancellous bone).

Each support component 61b may comprise any number of different heights, widths and depths so that a surgeon is able to pick the appropriate sized support component for the patient after intraoperative assessment and thereby avoid difficulties of size mismatch and bone graft contouring. A surgeon can use conventional measurement tools to select the size of each support component 65c. The size, position and orientation of each support component 61b is dependent on the size and location of the defects in the host bone as well as the quality of the bone that remains.

The support components 61b may be implanted in a bone as follows to form the periprosthetic support structure 60b. First, the acetabular cavity 15 of the hip bone 14 is inspected and tools (such as a reamer) may be used to clean material out of the acetabular cavity 15. Once the acetabular cavity 15 has been prepared, each support component 61b is impacted into or cemented onto the end portion 17 of the acetabular cavity 15 of the hip bone 14 in spaced apart relationship to form the periprosthetic support structure 60b. Preferably, each support component 61b is not cemented to the hip bone and therefore is available for bone ingrowth into the textured outer surface 63b of the support component 61b. The support components 61b may be arranged in any configuration that creates an access channel 68b that extends through the length of the periprosthetic support structure 60b. Preferably, the support components 61b are arranged to form a substantially hemispherical support structure. It can be seen that placement of the support components 65c precedes placement of any prosthetic joint components.

After the periprosthetic support structure 60b is constructed in a bone, the acetabular cup implant 36 may be placed into the access channel 68b of the periprosthetic support structure 60b. Placement can occur either during the same operative procedure as support component 61b placement or can be performed later once bone union to the support components 61b has occurred. In either instance, the acetabular cup implant 36 would be placed only after the acetabulum had been reconstructed using the support structure 60b. As shown in FIG. 23, at least a portion of the outer surface 37 of the acetabular cup implant 36 is secured to the inner surface 64b (shown in phantom) of the access channel 68b of the periprosthetic support structure 60b with a suitable adhesive such as bone cement 38 (e.g., polymethyl methacrylate). It can be seen that the periprosthetic support structure 60b does not extend beyond a plane defined by the end surface 18 of the end portion 17 of the hip bone 14.

Because the periprosthetic support structure 60b is not an integral component of the acetabular cup implant 36, the periprosthetic support structure 60b can be used with any acetabular cup implant 36 regardless of manufacturer or prosthetic design. Further, it should be noted that the example given in FIGS. 18 and 23 relates to use of the periprosthetic support structure 60b in the acetabular cavity of a hip bone; however, other common sites where the periprosthetic support structure 60b would be frequently used include the tibia and femur. Still other anatomic sites would include any joint that undergoes prosthetic arthroplasty when there is a significant metaphyseal bone deficiency.

Figure 19:
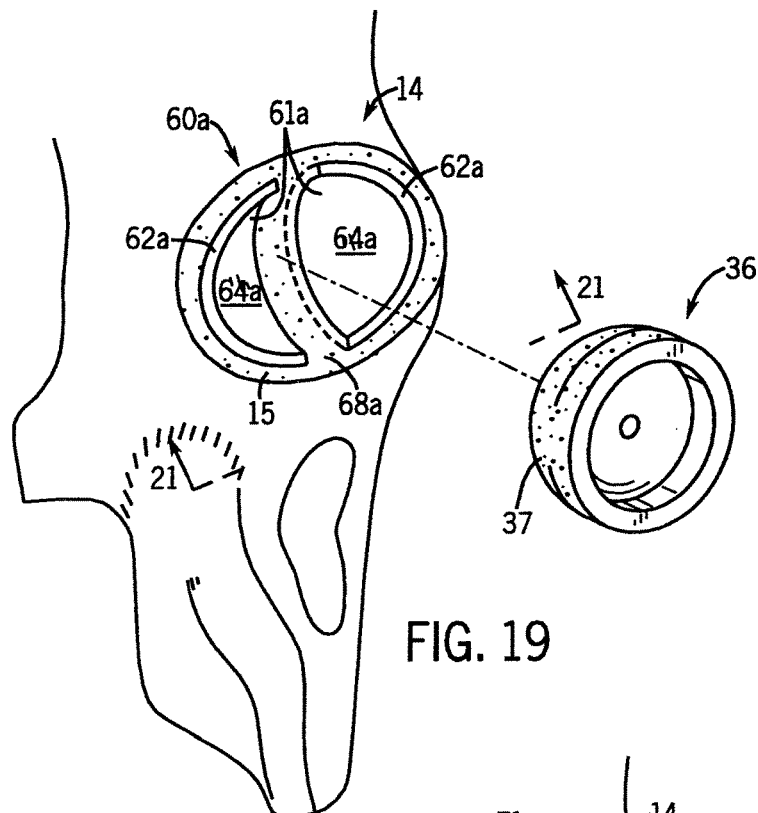
FIG. 19 is an exploded perspective view of an acetabular cup of a hip prosthesis being placed in yet another embodiment of a prosthetic implant support structure according to the invention secured in the acetabular cavity of a hip.
Figure 21:
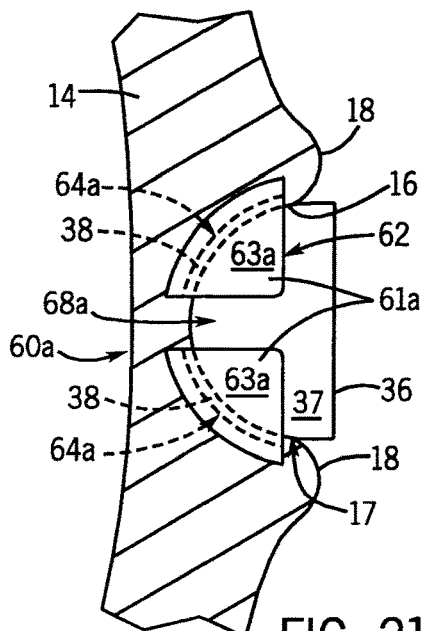
FIG. 21 is a cross-sectional view of an acetabular cup of a hip prosthesis placed in the prosthetic implant support structure of FIG. 19 taken along line 21-21 of FIG. 19.

Referring now to FIGS. 19 and 21, there is shown yet another prosthetic system according to the invention that includes an acetabular cup implant 36 having an outer surface 37 and a periprosthetic support structure, indicated generally at 60a, that is secured to the inner surface 16 of the acetabular cavity 15 of a hip bone 14. The periprosthetic support structure 60a comprises two support components 61a having a configuration approximating a quarter of a sphere. The support components 61a of the periprosthetic support structure 60a are impacted and/or cemented into the inner surface 16 of the acetabular cavity 15 of a hip bone 14 in a spaced apart relationship.

Each support component 61a may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, each support component 61a is formed from a metal alloy.

The outer surface 63a of each support component 61a may also be provided with a metallic texture coating which provides a textured surface so as to attain the desired fixation (by way of tissue ingrowth) between each support component 61a and the inner surface 16 of the acetabular cavity 15 of a hip bone 14 within which each support component 61a is implanted. The inner surface 64a of each support component 61a has a rough or corrugated surface finish to facilitate the interdigitation of bone cement. Likewise, the top end surface 62a of each support component 61a has a rough or corrugated surface finish to facilitate the interdigitation of bone cement.

Each support component 61a may comprise any number of different heights, widths and depths so that a surgeon is able to pick the appropriate sized support component for the patient after intraoperative assessment and thereby avoid difficulties of size mismatch and bone graft contouring. A surgeon can use conventional measurement tools to select the size of each support component 61a. The size, position and orientation of each support component 61a is dependent on the size and location of the defects in the host bone as well as the quality of the bone that remains.

The support components 61a may be implanted in a bone as follows to form the periprosthetic support structure 60a. First, the acetabular cavity 15 of the hip bone 14 is inspected and tools (such as a reamer) may be used to clean material out of the acetabular cavity 15. Once the acetabular cavity 15 has been prepared, each support component 61a is impacted into or cemented onto the end portion 17 of the acetabular cavity 15 of the hip bone 14 in spaced apart relationship to form the periprosthetic support structure 60a. Preferably, each support component 61a is not cemented to the hip bone and therefore is available for bone ingrowth into the textured outer surface 63a of the support component 61a. The support components 61a may be arranged in any configuration that creates an access channel 68a that extends through the length of the periprosthetic support structure 60a. Preferably, the support components 61a are arranged to form a substantially hemispherical support structure. It can be seen that placement of the support components 61a precedes placement of any prosthetic joint components.

After the periprosthetic support structure 60a is constructed in a bone, the acetabular cup implant 36 may be placed into the access channel 68a of the periprosthetic support structure 60a. Placement can occur either during the same operative procedure as support component 61a placement or can be performed later once bone union to the support components 61a has occurred. In either instance, the acetabular cup implant 36 would be placed only after the acetabulum had been reconstructed using the support structure 60a. As shown in FIG. 21, at least a portion of the outer surface 37 of the acetabular cup implant 36 is secured to the inner surface 64a (shown in phantom) of the access channel 68a of the periprosthetic support structure 60a with a suitable adhesive such as bone cement 38 (e.g., polymethyl methacrylate). It can be seen that the periprosthetic support structure 60a does not extend beyond a plane defined by the end surface 18 of the end portion 17 of the hip bone 14.

Because the periprosthetic support structure 60a is not an integral component of the acetabular cup implant 36, the periprosthetic support structure 60a can be used with any acetabular cup implant 36 regardless of manufacturer or prosthetic design. Further, it should be noted that the example given in FIGS. 19 and 21 relates to use of the periprosthetic support structure 60a in the acetabular cavity of a hip bone; however, other common sites where the periprosthetic support structure 60a would be frequently used include the tibia and femur. Still other anatomic sites would include any joint that undergoes prosthetic arthroplasty when there is a significant metaphyseal bone deficiency.

Figure 20:
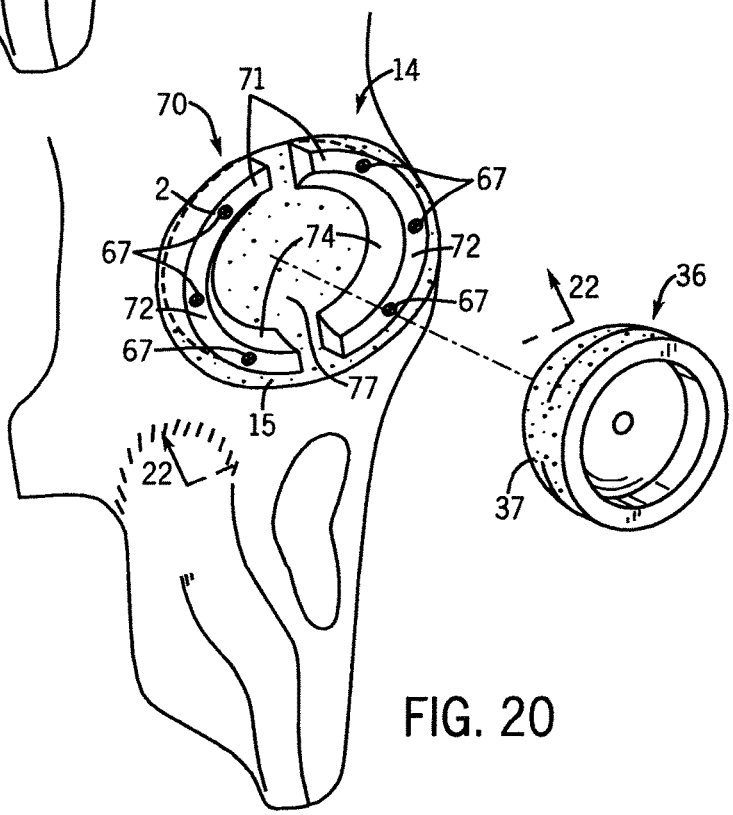
FIG. 20 is an exploded perspective view of an acetabular cup of a hip prosthesis being placed in still another embodiment of a prosthetic implant support structure according to the invention secured in the acetabular cavity of a hip.
Figure 22:
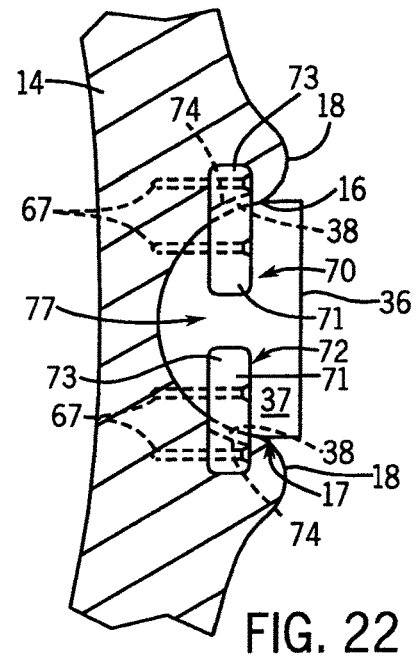
FIG. 22 is a cross-sectional view of an acetabular cup of a hip prosthesis placed in the prosthetic implant support structure of FIG. 20 taken along line 22-22 of FIG. 20.

Referring now to FIGS. 20 and 22, there is shown yet another prosthetic system according to the invention that includes an acetabular cup implant 36 having an outer surface 37 and a periprosthetic support structure, indicated generally at 70, that is secured to the inner surface 16 of the acetabular cavity 15 of a hip bone 14. The periprosthetic support structure 70 comprises two support components 71 having a configuration approximating a boomerang shape. The support components 71 of the periprosthetic support structure 70 are impacted, screwed and/or cemented into the inner surface 16 of the acetabular cavity 15 of a hip bone 14 in a spaced apart relationship.

Each support component 71 may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, each support component 71 is formed from a metal alloy.

The outer surface 73 of each support component 71 may also be provided with a metallic texture coating which provides a textured surface so as to attain the desired fixation (by way of tissue ingrowth) between each support component 71 and the inner surface 16 of the acetabular cavity 15 of a hip bone 14 within which each support component 71 is implanted. The inner surface 74 of each support component 71 has a rough or corrugated surface finish to facilitate the interdigitation of bone cement. Likewise, the top end surface 72 of each support component 71 has a rough or corrugated surface finish to facilitate the interdigitation of bone cement. Each support component 71 may comprise any number of different heights, widths and depths so that a surgeon is able to pick the appropriate sized support component for the patient after intraoperative assessment and thereby avoid difficulties of size mismatch and bone graft contouring. A surgeon can use conventional measurement tools to select the size of each support component 71.

The support components 71 may be implanted in a bone as follows to form the periprosthetic support structure 70. First, the acetabular cavity 15 of the hip bone 14 is inspected and tools (such as a reamer) may be used to clean material out of the acetabular cavity 15. Once the acetabular cavity 15 has been prepared, each support component 71 is placed into, impacted into, or cemented onto the end portion 17 of the acetabular cavity 15 of the hip bone 14 in spaced apart relationship to form the periprosthetic support structure 70. The support components 71 shown in FIGS. 20 and 22 are screwed into the hip bone 14 using screws 67 (shown in phantom in FIG. 22). The support components 71 may be arranged in any configuration that creates an access channel 77 that extends through the length of the periprosthetic support structure 70. The size, position and orientation of each support component 71 is dependent on the size and location of the defects in the host bone as well as the quality of the bone that remains.

After the periprosthetic support structure 70 is constructed in a bone, the acetabular cup implant 36 may be placed into the access channel 77 of the periprosthetic support structure

70. Placement can occur either during the same operative procedure as support component 71 placement or can be performed later once bone union to the support components 71 has occurred. In either instance, the acetabular cup implant 36 would be placed only after the acetabulum had been reconstructed using the support structure 70. As shown in FIG. 22, at least a portion of the outer surface 37 of the acetabular cup implant 36 is secured to the inner surface 74 (shown in phantom) of the access channel 77 of the periprosthetic support structure 70 with a suitable adhesive such as bone cement 38 (e.g., polymethyl methacrylate). It can be seen that the periprosthetic support structure 70 does not extend beyond a plane defined by the end surface 18 of the end portion 17 of the hip bone 14.

Because the periprosthetic support structure 70 is not an integral component of the acetabular cup implant 36, the periprosthetic support structure 70 can be used with any acetabular cup implant 36 regardless of manufacturer or prosthetic design. Further, it should be noted that the example given in FIGS. 20 and 22 relates to use of the periprosthetic support structure 70 in the acetabular cavity of a hip bone; however, other common sites where the periprosthetic support structure 70 would be frequently used include the tibia and femur. Still other anatomic sites would include any joint that undergoes prosthetic arthroplasty when there is a significant metaphyseal bone deficiency.

Therefore, the present invention provides prosthetic implant support structures that solve the problems associated with the loss of strong bone stock near a joint being replaced with a prosthesis. The described prosthetic implant support structures do not rely on the use of large amounts of bone graft or cumbersome bone graft delivery devices. The prosthetic implant support structures can eliminate the need to cement the distal portion of the stem of an implant to the inner surface of a bone cavity and can be used with a wide variety of prosthetic implants obtained from any number of different implant manufacturers. Furthermore, the described prosthetic implant system can optimize implant support on intact host bone with minimal removal of residual host bone and encourages bone ingrowth and attachment over as large a surface area as possible.

While the implantation of tibial, femoral, and acetabular prostheses has been illustrated and described herein, one skilled in the art will appreciate that the present invention can be practiced by other than the described embodiments, which have been presented for purposes of illustration and not of limitation. For instance, the methods and prostheses according to the invention can be used in the repair of any bone or in connection with the implantation of prosthetic devices at or in any bone in the body. Accordingly, the scope of the appended claims should not be limited to the description of the embodiments contained herein.

What is claimed is:

1. A method for supporting an acetabular cup implant and restoring lost bone stock in an acetabular cavity in a patient, the method comprising:
   implanting a partially-hemispherical support component and an acetabular cup implant in an acetabular cavity in a patient, wherein the partially-hemispherical support component provides support to the acetabular cup implant in the acetabular cavity with an adhesive located between an outer surface of the acetabular cup implant and an inner surface of the partially-hemispherical support component to secure the partially-hemispherical support component to the acetabular cup implant, said partially-hemispherical support component consisting essentially of a porous metal material that is a bone ingrowth-receptive material with a porous structure for encouraging bone ingrowth and attachment throughout the partially-hemispherical support component for restoring lost bone stock in the acetabular cavity, said partially-hemispherical support component including a convex outer surface facing an inner surface of the acetabular cavity and providing a surface through which bone of the patient can grow into said partially-hemispherical support component, wherein the partially-hemispherical support component is formed separately from said acetabular cup implant for subsequent connection to said acetabular cup implant, and wherein the partially-hemispherical support component is capable of being positioned, by itself, in the acetabular cavity prior to being secured to said acetabular cup implant and is capable of being impacted, by itself, into the acetabular cavity for obtaining a press fit of the partially-hemispherical support component in the acetabular cavity.

2. The method of claim 1, wherein said partially-hemispherical support component has an established size and shape after formation and prior to being secured to said acetabular cup implant, said established size and shape including the convex outer surface of the partially-hemispherical support component.

3. The method of claim 1, wherein said partially-hemispherical support component has an established size and shape after formation and prior to being secured to said acetabular cup implant, the established size and shape of the partially-hemispherical support component including an external geometry that is implantable in the acetabular cavity, and wherein said implanting includes impacting the partially-hemispherical support component into the acetabular cavity and obtaining a press fit of said external geometry in the acetabular cavity despite the partially-hemispherical support component consisting essentially of said porous metal material.

4. The method of claim 2, wherein the partially-hemispherical support component has a shape approximating a quarter of a sphere.

5. The method of claim 1, wherein the partially-hemispherical support component includes a screw hole for securing the partially-hemispherical support component to the inner surface of the acetabular cavity.

6. The method of claim 1, wherein the partially-hemispherical support component includes a fenestration that can be filled with a bone graft material and which extends fully through the partially-hemispherical support component from said convex outer surface to said inner surface.

7. The method of claim 1, wherein the inner surface of the partially-hemispherical support component includes a corrugated surface finish.

8. The method of claim 1, wherein the partially-hemispherical support component is formed with a metal alloy.

9. The method of claim 8, wherein the partially-hemispherical support component is formed with a titanium alloy.

10. A method for supporting an acetabular cup implant and restoring lost bone stock in an acetabular cavity in a patient, the method comprising:
    implanting a support component and an acetabular cup implant in an acetabular cavity in a patient, wherein the support component provides support to the acetabular cup implant in the acetabular cavity, the support component consisting essentially of a porous metal material that is a bone ingrowth-receptive material with a porous structure for encouraging bone ingrowth and attachment throughout the support component for restoring lost bone stock in the acetabular cavity, said support component including a convex outer surface facing an inner surface of the acetabular cavity and providing a surface through which bone of the patient can grow into said support component and including an inner surface accommodating an outer surface of the acetabular cup implant, wherein the support component is formed separately from said acetabular cup implant for subsequent connection to said acetabular cup implant, and wherein the support component is capable of being positioned, by itself, in the acetabular cavity prior to being secured to said acetabular cup implant and is capable of being impacted, by itself, into the acetabular cavity for obtaining a press fit of the support component in the acetabular cavity, wherein the support component is connected to the acetabular cup implant, the support component having an established size and shape after formation and prior to being connected to the acetabular cup implant, said established size and shape of the support component including an external geometry that is implantable in the acetabular cavity, and wherein said implanting includes impacting the support component into the acetabular cavity and obtaining a press fit of said external geometry in the acetabular cavity despite the support component consisting essentially of said porous metal material.

11. A method for supporting an acetabular cup implant and restoring lost bone stock in an acetabular cavity in a patient, the method comprising:

implanting a support component and an acetabular cup implant in an acetabular cavity in a patient, wherein the support component provides support to the acetabular cup implant in the acetabular cavity, the support component consisting essentially of a porous metal material that is a bone ingrowth-receptive material with a porous structure for encouraging bone ingrowth and attachment throughout the support component for restoring lost bone stock in the acetabular cavity, said support component including a convex outer surface facing an inner surface of the acetabular cavity and providing a surface through which bone of the patient can grow into said support component and including an inner surface accommodating an outer surface of the acetabular cup implant, wherein the support component is formed separately from said acetabular cup implant for subsequent connection to said acetabular cup implant, and wherein the support component is capable of being positioned, by itself, in the acetabular cavity prior to being secured to said acetabular cup implant and is capable of being impacted, by itself, into the acetabular cavity for obtaining a press fit of the support component in the acetabular cavity, wherein said inner surface of the support component accommodates only a portion of the outer surface of the acetabular cup implant.

12. The method of claim 11, wherein an adhesive is located between the inner surface of the support component and the outer surface of the acetabular cup implant.

13. A method for supporting an acetabular cup implant and restoring lost bone stock in an acetabular cavity in a patient, the method comprising:

implanting a support component and an acetabular cup implant in an acetabular cavity in a patient, wherein the support component provides support to the acetabular cup implant in the acetabular cavity, the support component consisting essentially of a porous metal material that is a bone ingrowth-receptive material with a porous structure for encouraging bone ingrowth and attachment throughout the support component for restoring lost bone stock in the acetabular cavity, said support component including a convex outer surface facing an inner surface of the acetabular cavity and providing a surface through which bone of the patient can grow into said support component and including an inner surface accommodating an outer surface of the acetabular cup implant, wherein the support component is formed separately from said acetabular cup implant for subsequent connection to said acetabular cup implant, and wherein the support component is capable of being positioned, by itself, in the acetabular cavity prior to being secured to said acetabular cup implant and is capable of being impacted, by itself, into the acetabular cavity for obtaining a press fit of the support component in the acetabular cavity, wherein the support component has a shape approximating a quarter of a sphere.

14. The method of claim 12, wherein the inner surface of the support component includes a rough or corrugated surface finish into which said adhesive interdigitates.

15. A method of implantation in an acetabular cavity in a patient, the method comprising:

implanting a formed partially-hemispherical porous body in an acetabular cavity in a patient, said partially-hemispherical porous body including a convex outer surface facing an inner surface of the acetabular cavity and an inner surface suitable for accommodating an outer surface of an acetabular cup implant, wherein said partially-hemispherical porous body is positionable, by itself, in the acetabular cavity and is capable of being impacted, by itself, into the acetabular cavity for obtaining a press fit of the partially-hemispherical porous body in the acetabular cavity, wherein the partially-hemispherical porous body consists essentially of a porous metal material that is a bone ingrowth-receptive material with a porous structure for allowing bone of the patient to grow into the porous body through the convex outer surface of the porous body and for encouraging bone ingrowth and attachment throughout the porous body for restoring lost bone stock in the acetabular cavity.

16. The method of claim 15, wherein said partially-hemispherical porous body includes a screw hole for securing the partially-hemispherical porous body to the inner surface of the acetabular cavity.

17. The method of claim 15 further comprising positioning part of an acetabular cup implant in an interior of the porous body with the inner surface of the partially-hemispherical porous body accommodating an outer surface of the acetabular cup implant.

18. The method of claim 15, wherein said partially-hemispherical porous body has an external geometry implantable in the acetabular cavity, and wherein said implanting includes impacting the partially-hemispherical porous body into the acetabular cavity and obtaining a press fit of said external geometry in the acetabular cavity despite the partially-hemispherical porous body consisting essentially of said porous metal material.

19. The method of claim 15, wherein said partially-hemispherical porous body includes a fenestration that can be filled with a bone graft material and which extends fully through the partially-hemispherical porous body from said convex outer surface to said inner surface.

20. The method of claim 15, wherein the inner surface of the partially-hemispherical porous body includes a corrugated surface finish.

21. The method of claim 15, wherein said partially-hemispherical porous body is formed with a metal alloy.

22. The method of claim 21, wherein said partially-hemispherical porous body is formed with a titanium alloy.

23. A method for supporting an acetabular cup implant and restoring lost bone stock in an acetabular cavity in a patient, the method comprising:
    implanting a porous support component and an acetabular cup implant in an acetabular cavity in a patient, wherein said porous support component provides support to the acetabular cup implant in the acetabular cavity with a bone cement located between a convex outer surface of the acetabular cup implant and a concave inner surface of the porous support component to secure the porous support component to the acetabular cup implant, and wherein said implanting includes impacting the porous support component into the acetabular cavity and obtaining a press fit of said porous support component in the acetabular cavity despite said porous support component consisting essentially of a porous metal material that is a bone ingrowth-receptive material with a porous structure for encouraging bone ingrowth and attachment throughout the porous support component for restoring lost bone stock in the acetabular cavity, said porous support component including a convex outer surface facing an inner surface of the acetabular cavity and providing a surface through which bone of the patient can grow into said porous support component, wherein the porous support component is formed separately from said acetabular cup implant for subsequent connection to said acetabular cup implant and is capable of being impacted, by itself, into the acetabular cavity for obtaining said press fit prior to being secured to said acetabular cup implant,
    wherein the porous support component has an external geometry implantable in the acetabular cavity, and wherein said implanting includes impacting the porous support component into the acetabular cavity and obtaining a press fit of said external geometry in the acetabular cavity despite the porous support component consisting essentially of said porous metal material.

24. The method of claim 15, wherein said partially-hemispherical porous body has a shape approximating a quarter of a sphere.

25. The method of claim 1, wherein said partially-hemispherical support component is formed entirely with said porous metal material.

26. The method of claim 15, wherein said partially-hemispherical porous body is formed entirely with said porous metal material.

27. The method of claim 18, wherein said partially-hemispherical porous body has an established size and shape prior to said implanting.

28. A method for supporting an acetabular cup implant and restoring lost bone stock in an acetabular cavity in a patient, the method comprising:
    implanting a porous support component and an acetabular cup implant in an acetabular cavity in a patient, wherein said porous support component provides support to the acetabular cup implant in the acetabular cavity with a bone cement located between a convex outer surface of the acetabular cup implant and a concave inner surface of the porous support component to secure the porous support component to the acetabular cup implant, and wherein said implanting includes impacting the porous support component into the acetabular cavity and obtaining a press fit of said porous support component in the acetabular cavity despite said porous support component consisting essentially of a porous metal material that is a bone ingrowth-receptive material with a porous structure for encouraging bone ingrowth and attachment throughout the porous support component for restoring lost bone stock in the acetabular cavity, said porous support component including a convex outer surface facing an inner surface of the acetabular cavity and providing a surface through which bone of the patient can grow into said porous support component, wherein the porous support component is formed separately from said acetabular cup implant for subsequent connection to said acetabular cup implant and is capable of being impacted, by itself, into the acetabular cavity for obtaining said press fit prior to being secured to said acetabular cup implant,
    wherein said porous support component is formed entirely with said porous metal material.

29. The method of claim 23, wherein said porous support component has an established size and shape prior to being secured to said acetabular cup implant.

30. The method of claim 1 performed as part of an acetabular revision surgery, wherein the acetabular cup implant is a replacement acetabular cup implant.

31. A method for supporting an acetabular cup implant and restoring lost bone stock in an acetabular cavity in a patient, the method comprising:
    implanting a support component and an acetabular cup implant in an acetabular cavity in a patient, wherein the support component provides support to the acetabular cup implant in the acetabular cavity, the support component consisting essentially of a porous metal material that is a bone ingrowth-receptive material with a porous structure for encouraging bone ingrowth and attachment throughout the support component for restoring lost bone stock in the acetabular cavity, said support component including a convex outer surface facing an inner surface of the acetabular cavity and providing a surface through which bone of the patient can grow into said support component and including an inner surface accommodating an outer surface of the acetabular cup implant, wherein the support component is formed separately from said acetabular cup implant for subsequent connection to said acetabular cup implant, and wherein the support component is capable of being positioned, by itself, in the acetabular cavity prior to being secured to said acetabular cup implant and is capable of being impacted, by itself, into the acetabular cavity for obtaining a press fit of the support component in the acetabular cavity,
    wherein the support component is connected to the acetabular cup implant, the support component having an established size and shape after formation and prior to being connected to the acetabular cup implant, said established size and shape including the convex outer surface of the support component.

32. A method for supporting an acetabular cup implant and restoring lost bone stock in an acetabular cavity in a patient, the method comprising:
    implanting a support component and an acetabular cup implant in an acetabular cavity in a patient, wherein the support component provides support to the acetabular cup implant in the acetabular cavity, the support component consisting essentially of a porous metal material that is a bone ingrowth-receptive material with a porous structure for encouraging bone ingrowth and attachment throughout the support component for restoring lost bone stock in the acetabular cavity, said support component including a convex outer surface facing an inner surface of the acetabular cavity and providing a surface through which bone of the patient can grow into said support component and including an inner surface accommodating an outer surface of the acetabular cup implant, wherein the support component is formed separately from said acetabular cup implant for subsequent connection to said acetabular cup implant, and wherein the support component is capable of being positioned, by itself, in the acetabular cavity prior to being secured to said acetabular cup implant and is capable of being impacted, by itself, into the acetabular cavity for obtaining a press fit of the support component in the acetabular cavity, wherein the support component being formed separately from the acetabular cup implant for subsequent connection to the acetabular cup implant includes the support component being formed with an external geometry that includes said convex outer surface, and wherein the support component, despite consisting essentially of the porous metal material, is capable of being impacted, by itself, into the acetabular cavity for obtaining a press fit of said convex outer surface in the acetabular cavity.

33. The method of claim 15 further comprising connecting the formed partially-hemispherical porous body to an acetabular cup implant, the formed partially-hemispherical porous body having an established size and shape prior to being connected to the acetabular cup implant, said established size and shape including the convex outer surface of the formed partially-hemispherical porous body.

34. The method of claim 15, wherein the formed partially-hemispherical porous body has an external geometry implantable in the acetabular cavity, and wherein the formed partially-hemispherical porous body, despite consisting essentially of said porous metal material, is capable of being impacted, by itself, into the acetabular cavity for obtaining a press fit of said external geometry in the acetabular cavity.

35. The method of claim 15, wherein the formed partially-hemispherical porous body is formed with an external geometry that includes said convex outer surface, and wherein the formed partially-hemispherical porous body, despite consisting essentially of the porous metal material, is capable of being impacted, by itself, into the acetabular cavity for obtaining a press fit of said convex outer surface in the acetabular cavity.

\* \* \* \* \*